(12) United States Patent
Abele et al.

(10) Patent No.: US 9,556,125 B2
(45) Date of Patent: Jan. 31, 2017

(54) PROCESS FOR PREPARING A PYRIMIDINE INTERMEDIATE

(71) Applicant: ACTELION PHARMACEUTICALS LTD, Allschwil (CH)

(72) Inventors: Stefan Abele, Allschwil (CH); Jacques-Alexis Funel, Allschwil (CH); Ivan Schindelholz, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/904,657

(22) PCT Filed: Jul. 11, 2014

(86) PCT No.: PCT/EP2014/064904
§ 371 (c)(1),
(2) Date: Jan. 12, 2016

(87) PCT Pub. No.: WO2015/004265
PCT Pub. Date: Jan. 15, 2015

(65) Prior Publication Data
US 2016/0145215 A1 May 26, 2016

(30) Foreign Application Priority Data

Jul. 12, 2013 (EP) .................................. 13176374

(51) Int. Cl.
*C07D 239/47* (2006.01)
*C07D 239/34* (2006.01)
*C07D 239/30* (2006.01)

(52) U.S. Cl.
CPC ........... *C07D 239/47* (2013.01); *C07D 239/30* (2013.01)

(58) Field of Classification Search
USPC .................................................. 544/319, 327
See application file for complete search history.

(56) References Cited

U.S. PATENT DOCUMENTS 7,094,781 B2    8/2006 Bolli et al.

OTHER PUBLICATIONS

Bolli, et al., "The Discovery of N-[5-(4-Bromophenyl)-6-[2-[(5-bromo-2-pyrimidinyl)oxy]ethoxy]-4-pyrimidinyl]-N'-propylsulfamide (Macitentan), an Orally Active, Potent Dual Endothelin Receptor Antagonist" J. Med. Chem., Aug. 2012, vol. 55, pp. 7849-7861.
International Search Report of International Application No. PCT/EP2014/064904, mailed Aug. 1, 2014.

*Primary Examiner* — Charanjit Aulakh
(74) *Attorney, Agent, or Firm* — Hoxie & Associates LLC

(57) ABSTRACT

The invention relates to a process for preparing a pyrimidine intermediate, namely the compound of formula I-2

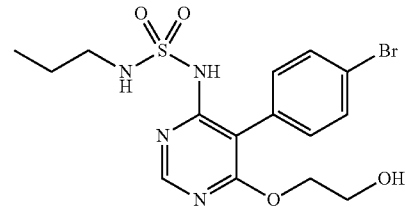

I-2 or a salt thereof, which involves the use of a liquid-liquid extraction using methyl iso-butyl ketone. Said compound of formula I-2 or its salt can be used to prepare macitentan.

12 Claims, No Drawings

PROCESS FOR PREPARING A PYRIMIDINE INTERMEDIATE

CROSS-REFERENCE TO RELATED APPLICATIONS

This application is a National Stage Entry of International Application No. PCT/EP2014/064904, filed on Jul. 11, 2014, which claims priority from European Patent Application No. 13176374.0, filed on Jul. 12, 2013, the contents of each of which are hereby incorporated by reference in their entirety.

The present invention relates to a process for preparing a pyrimidine intermediate, namely the compound of formula I-2

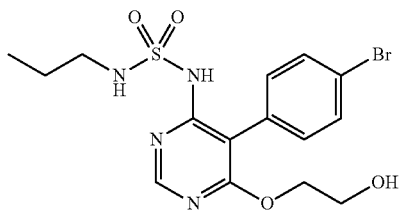

or a salt thereof. Said compound of formula I-2 or its salt can be used to prepare macitentan.

Macitentan (chemical names: N-[5-(4-bromophenyl)-6-[2-[(5-bromo-2-pyrimidinyl)oxy]ethoxy]-4-pyrimidinyl]-N'-propylsulfamide or N-[5-(4-bromophenyl)-6-{2-[(5-bromopyrimidin-2-yl)oxy]ethoxy}pyrimidin-4-yl]-N'-propylsulfuric diamide) is an endothelin receptor antagonist that has notably been approved by the US Food and Drug Administration and the European Commission for the treatment of pulmonary arterial hypertension. It has been first disclosed in WO 02/053557. The last step of one of the potential preparation routes described in WO 02/053557, called "Possibility A" and "Possibility B", can be summarised as shown in Scheme A1 hereafter.

Scheme A1

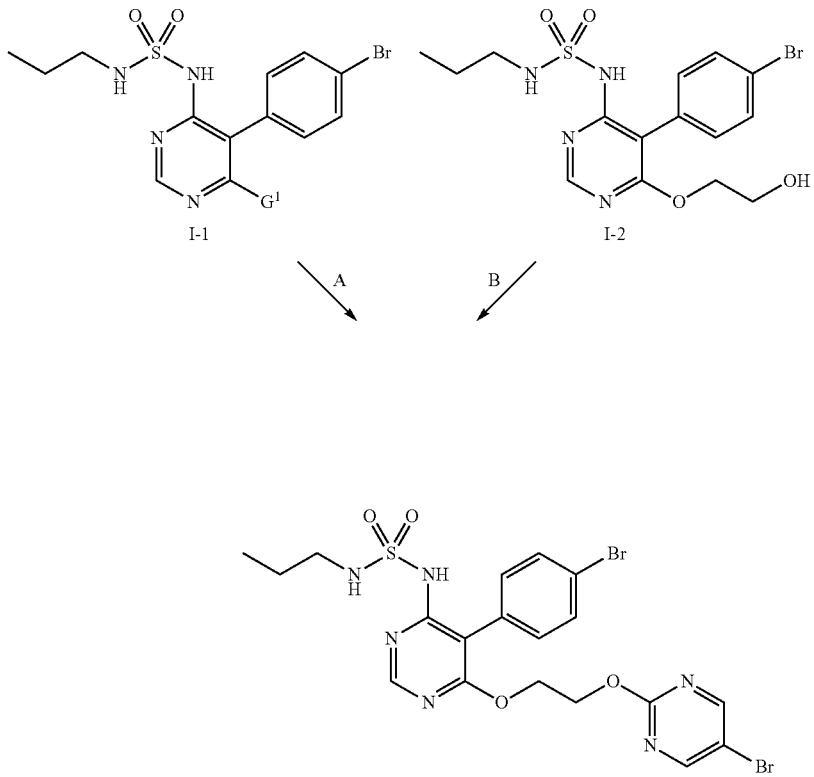

In Scheme A1, G¹ represents a reactive residue, and preferentially a chloro atom.

The preparation of macitentan according to "Possibility B" of WO 02/053557 has furthermore been described in Bolli et al., *J. Med. Chem.* (2012), 55, 7849-7861. Accordingly:

KOtBu was added to a solution of ethylene glycol in dimethoxyethane and the compound of formula I-1 wherein G¹ is Cl (see Scheme A1 above) was added thereto; after heating at 100° C. for 70 h, work-up involving extraction and purification by column chromatography, the compound of formula I-2 was obtained in a 86% yield; and The compound of formula I-2 was added to a suspension of NaH in THF, the mixture was stirred and diluted with DMF before 5-bromo-2-chloropyrimidine was added; after heating at 60° C. and work-up involving extraction and crystallisation steps, macitentan was obtained in a 88% yield.

As an alternative to the first step of the method described by Bolli et al., the compound of formula I-1 wherein G¹ is Cl could be mixed with an excess of ethylene glycol (about 30-50 equivalents), an excess of tBuOK (3-4 equivalents)

could be added and the resulting mixture could be heated to 100° C. After addition of water and MeOH and pH adjustment with HCl, the compound of formula I-2 could then be filtered off and obtained, after drying under vacuum, in an about 85% yield.

The methods for manufacturing macitentan described above are however not appropriate for manufacturing macitentan in a sufficient purity unless numerous purification steps are undertaken to remove the impurities from the compound of formula I-2 before performing the step corresponding to "Possibility B" of WO 02/053557. In this regard, it should be mentioned that ethylene glycol is actually harmful and rather difficult to remove by distillation due to a high boiling point.

In order to avoid significant formation of by-product in the last step of the process for manufacturing macitentan, the amount of ethylene glycol in the compound of formula I-2 must be below 2500 ppm. This threshold can only be reached by the use of several filtrations and repeated washings with MeOH/water, which increases the overall cost and cycle time of the process.

It has now been surprisingly found that the reaction of the compound of formula I-1 wherein $G^1$ is Cl with an excess of ethylene glycol could be significantly improved by the use of a specific solvent, MIBK. The use of MIBK allows complete removal of ethylene glycol by simple extractive work-up (from water, under homogeneous liquid-liquid conditions instead of solid-liquid as performed otherwise), thereby eliminating the need for multiple washings and filtrations. Besides, it has been found that the use of MIBK as solvent may allow to reduce the amount of equivalents of ethylene glycol to be used so as to obtain an appropriate yield and purity of the compound of formula I-2. These results for MIBK are unexpected since similar ketone solvents either do not allow sufficient ethylene glycol removal or bring about stability or work-up issues (see Reference Examples).

Various embodiments of the invention are presented hereafter:

1) The invention firstly relates to a process for manufacturing the compound of formula I-2

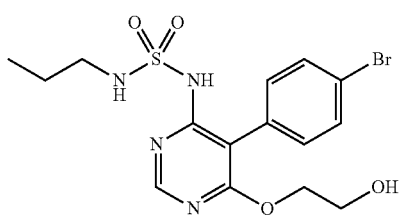

I-2 said process comprising the reaction of the compound of formula I-1

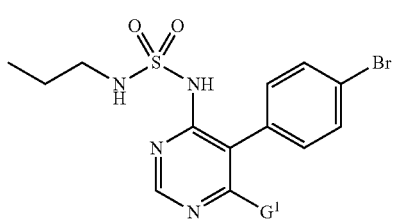

I-1 wherein $G^1$ represents halogen, or a salt of said compound, with ethylene glycol in the presence of a base, CHARACTERISED IN THAT, after the compound of formula I-2 has been obtained, a liquid-liquid extraction is performed, whereby methyl iso-butyl ketone is used to extract the compound of formula I-2 from an aqueous phase containing the products of the reaction of the compound of formula I-1 with ethylene glycol.

2) Preferably, the compound of formula I-1 used in the process according to embodiment 1) will be such that $G^1$ represents chlorine.

3) Preferably also, the base used in the process according to embodiment 1) or 2) will be selected from the group consisting of NaOH, KOH and potassium tert-butylate.

4) In particular, the base used in the process according to embodiment 1) or 2) will be potassium tert-butylate.

5) Preferably, the pH of the aqueous phase from which the compound of formula I-2 is extracted according to the process according to one of embodiments 1) to 4) will be between 3 and 5.

6) Besides, the reaction of the compound of formula I-1 with ethylene glycol according to one of embodiments 1) to 5) will preferably be such that 20 to 50 equivalents of ethylene glycol are used per equivalent of compound of formula I-1.

7) In particular, the reaction of the compound of formula I-1 with ethylene glycol according to embodiment 6) can be such that 25 to 40 equivalents of ethylene glycol are used per equivalent of compound of formula I-1.

8) Preferably, to ensure that the pH of the aquous phase from which the compound of formula I-2 is extracted according to the process of one of embodiments 5) to 7) is between 3 and 5, a solution of hydrochloric acid or citric acid in water will be used.

9) More preferably, in the process according to embodiment 8), a solution of citric acid in water will be used to ensure that the pH of the aqueous phase from which the compound of formula I-2 is extracted is between 3 and 5.

10) Preferably also, in the process according to one of embodiments 1) to 9), the reaction of the compound of formula I-1 with ethylene glycol will be performed in methyl iso-butyl ketone.

11) Preferably, in the process according to embodiment 10), the volume of methyl iso-butyl ketone used for performing the reaction of the compound of formula I-1 with ethylene glycol will be from 3 to 7 times the volume of ethylene glycol.

12) More preferably, in the process according to embodiment 11), the volume of methyl iso-butyl ketone used for performing the reaction of the compound of formula I-1 with ethylene glycol will be from 4 to 6 times the volume of ethylene glycol.

13) According to a particular variant of this invention, the process according to one of embodiments 10) to 12) will be performed using 3 to 20 equivalents of ethylene glycol per equivalent of compound of formula I-1.

14) In particular, the process according to embodiment 13) will be performed using 5 to 7 equivalents of ethylene glycol per equivalent of compound of formula I-1.

15) Pursuant to a preferred method for performing the liquid-liquid extraction of the process according to one of embodiments 1) to 14), the mixture of the aqueous phase and the organic phase is heated to a temperature from 35 to 60° C. before the phases are separated.

16) Preferably, in the preferred method according to embodiment 15), the mixture of the aqueous phase and the organic phase is heated to a temperature from 45 to 55° C. before the phases are separated.

17) According to a further variant of this invention, the compound of formula I-2 obtained following a process according to any of embodiments 1) to 16) is crystallised by partial evaporation of methyl iso-butyl ketone from the organic phase collected, addition of an apolar aprotic organic solvent or of a mixture of apolar aprotic organic solvents to said organic phase, heating of the mixture thus obtained until complete solid dissolution is achieved and cooling down the mixture to obtain crystallisation of the compound of formula I-2.

18) Preferably, in the process according to embodiment 17), the compound of formula I-2 obtained following a process according to any of embodiments 1) to 16) is crystallised by partial evaporation of methyl iso-butyl ketone from the organic phase collected, addition of heptane to said organic phase, heating of the mixture thus obtained until complete solid dissolution is achieved and cooling down the mixture to obtain crystallisation of the compound of formula I-2.

19) Preferably, the volume of methyl iso-butyl ketone evaporated from the organic phase collected in the process according to embodiment 18) will be from 20 to 50 percent of the total volume of methyl iso-butyl ketone.

20) Preferably, the volume of heptane added to the organic phase in the process according to embodiment 18) or 19) will be from 1 to 3 times the volume of the organic phase.

21) More preferably, the volume of heptane added to the organic phase in the process according to embodiment 18) or 19) will be from 1.5 to 2.5 times the volume of the organic phase.

22) Preferably, the manufacturing process according to one of embodiments 1) to 21) will be such that the proportion of residual ethylene glycol in the compound of formula I-2 obtained (as measured by the ion chromatography method described in the "Examples" section) is below 500 ppm.

23) More preferably, the manufacturing process according to one of embodiments 1) to 21) will be such that the proportion of residual ethylene glycol in the compound of formula I-2 obtained (as measured by the ion chromatography method described in the "Examples" section) is below 200 ppm.

24) Even more preferably, the manufacturing process according to one of embodiments 1) to 21) will be such that the proportion of residual ethylene glycol in the compound of formula I-2 obtained (as measured by the ion chromatography method described in the "Examples" section) is below 100 ppm.

25) This invention furthermore relates to the use of methyl iso-butyl ketone for removing ethylene glycol from the compound of formula I-2 as defined in embodiment 1) when said compound is obtained by the reaction of the compound of formula I-1 as defined in embodiment 1) with ethylene glycol in the presence of a base.

26) This invention in particular relates to the use of methyl iso-butyl ketone for removing ethylene glycol from the compound of formula I-2 as defined in embodiment 1) when said compound is obtained by the reaction of the compound of formula I-1 as defined in embodiment 2) with ethylene glycol in the presence of a base.

27) Preferably, the base used in embodiment 25) or 26) will be selected from the group consisting of NaOH, KOH and potassium tert-butylate.

28) More preferably, the base used in embodiment 25) or 26) will be potassium tert-butylate.

29) Preferably, the use of methyl iso-butyl ketone according to one of embodiments 25) to 28) will be such that the proportion of residual ethylene glycol in the compound of formula I-2 obtained following said use (as measured by the ion chromatography method described in the "Examples" section) is below 500 ppm.

30) More preferably, the use of methyl iso-butyl ketone according to one of embodiments 25) to 28) will be such that the proportion of residual ethylene glycol in the compound of formula I-2 obtained following said use (as measured by the ion chromatography method described in the "Examples" section) is below 200 ppm.

31) Even more preferably, the use of methyl iso-butyl ketone according to one of embodiments 25) to 28) will be such that the proportion of residual ethylene glycol in the compound of formula I-2 obtained following said use (as measured by the ion chromatography method described in the "Examples" section) is below 100 ppm.

This invention thus notably relates to the manufacturing processes and the uses as defined in one of embodiments 1) and 25) or to these manufacturing processes and uses further limited under consideration of their respective dependencies by the characteristics of any one of embodiments 2) to 24) and 26) to 31). In particular, based on the dependencies of the different embodiments as disclosed hereinabove, the following manufacturing process and use embodiments are thus possible and intended and herewith specifically disclosed in individualized form: 1, 2+1, 3+1, 3+2+1, 4+1, 4+2+1, 5+2+1, 5+4+1, 5+4+2+1, 6+2+1, 6+4+1, 6+4+2+1, 6+5+2+1, 6+5+4+1, 6+5+4+2+1, 7+6+2+1, 7+6+4+1, 7+6+4+2+1, 7+6+5+2+1, 7+6+5+4+1, 7+6+5+4+2+1, 8+2+1, 8+4+1, 8+4+2+1, 8+5+2+1, 8+5+4+1, 8+5+4+2+1, 8+7+6+2+1, 8+7+6+4+1, 8+7+6+4+2+1, 8+7+6+5+2+1, 8+7+6+5+4+1, 8+7+6+5+4+2+1, 9+8+2+1, 9+8+4+1, 9+8+4+2+1, 9+8+5+2+1, 9+8+5+4+1, 9+8+5+4+2+1, 9+8+7+6+2+1, 9+8+7+6+4+1, 9+8+7+6+4+2+1, 9+8+7+6+5+2+1, 9+8+7+6+5+4+1, 9+8+7+6+5+4+2+1, 10+2+1, 10+4+1, 10+4+2+1, 10+5+2+1, 10+5+4+1, 10+5+4+2+1, 10+8+2+1, 10+8+4+1, 10+8+4+2+1, 10+8+5+2+1, 10+8+5+4+1, 10+8+5+4+2+1, 10+8+7+6+2+1, 10+8+7+6+4+1, 10+8+7+6+4+2+1, 10+8+7+6+5+2+1, 10+8+7+6+5+4+1, 10+8+7+6+5+4+2+1, 11+10+2+1, 11+10+4+1, 11+10+4+2+1, 11+10+5+2+1, 11+10+5+4+1, 11+10+5+4+2+1, 11+10+8+2+1, 11+10+8+4+1, 11+10+8+4+2+1, 11+10+8+5+2+1, 11+10+8+5+4+1, 11+10+8+5+4+2+1, 11+10+8+7+6+2+1, 11+10+8+7+6+4+1, 11+10+8+7+6+4+2+1, 11+10+8+7+6+5+2+1, 11+10+8+7+6+5+4+1, 11+10+8+7+6+5+4+2+1, 12+11+10+2+1, 12+11+10+4+1, 12+11+10+4+2+1, 12+11+10+5+2+1, 12+11+10+5+4+1, 12+11+10+5+4+2+1, 12+11+10+8+2+1, 12+11+10+8+4+1, 12+11+10+8+4+2+1, 12+11+10+8+5+2+1, 12+11+10+8+5+4+1, 12+11+10+8+5+4+2+1, 12+11+10+8+7+6+2+1, 12+11+10+8+7+6+4+1, 12+11+10+8+7+6+4+2+1, 12+11+10+8+7+6+5+2+1, 12+11+10+8+7+6+5+4+1, 12+11+10+8+7+6+5+4+2+1, 13+10+2+1, 13+10+4+1, 13+10+4+2+1, 13+10+5+2+1, 13+10+5+4+1, 13+10+5+4+2+1, 13+10+8+2+1, 13+10+8+4+1, 13+10+8+4+2+1, 13+10+8+5+2+1, 13+10+8+5+4+1, 13+10+8+5+4+2+1, 13+10+8+7+6+2+1, 13+10+8+7+6+4+1, 13+10+8+7+6+4+2+1, 13+10+8+7+6+5+2+1, 13+10+8+7+6+5+4+1, 13+10+8+7+6+5+4+2+1, 13+12+11+10+2+1, 13+12+11+10+4+1, 13+12+11+10+4+2+1, 13+12+11+10+5+2+1, 13+12+11+10+5+4+1, 13+12+11+10+5+4+2+1, 13+12+11+10+8+2+1, 13+12+11+10+8+4+1, 13+12+11+10+8+4+2+1, 13+12+11+10+8+5+2+1, 13+12+11+10+8+5+4+1, 13+12+11+10+8+5+4+2+1, 13+12+11+10+8+7+6+2+1, 13+12+11+10+8+

7+6+4+1, 13+12+11+10+8+7+6+4+2+1, 13+12+11+10+8+ 7+6+5+2+1, 13+12+11+10+8+7+6+5+4+1, 13+12+11+10+ 8+7+6+5+4+2+1, 14+13+10+2+1, 14+13+10+4+1, 14+13+ 10+4+2+1, 14+13+10+5+2+1, 14+13+10+5+4+1, 14+13+ 10+5+4+2+1, 14+13+10+8+2+1, 14+13+10+8+4+1, 14+13+10+8+4+2+1, 14+13+10+8+5+2+1, 14+13+10+8+ 5+4+1, 14+13+10+8+5+4+2+1, 14+13+10+8+7+6+2+1, 14+13+10+8+7+6+4+1, 14+13+10+8+7+6+4+2+1, 14+13+ 10+8+7+6+5+2+1, 14+13+10+8+7+6+5+4+1, 14+13+10+ 8+7+6+5+4+2+1, 14+13+12+11+10+2+1, 14+13+12+11+ 10+4+1, 14+13+12+11+10+4+2+1, 14+13+12+11+10+5+ 2+1, 14+13+12+11+10+5+4+1, 14+13+12+11+10+5+4+2+ 1, 14+13+12+11+10+8+2+1, 14+13+12+11+10+8+4+1, 14+13+12+11+10+8+4+2+1, 14+13+12+11+10+8+5+2+1, 14+13+12+11+10+8+5+4+1, 14+13+12+11+10+8+5+4+2+ 1, 14+13+12+11+10+8+7+6+2+1, 14+13+12+11+10+8+7+ 6+4+1, 14+13+12+11+10+8+7+6+4+2+1, 14+13+12+11+ 10+8+7+6+5+2+1, 14+13+12+11+10+8+7+6+5+4+1, 14+13+12+11+10+8+7+6+5+4+2+1, 15+2+1, 15+4+1, 15+4+2+1, 15+5+2+1, 15+5+4+1, 15+5+4+2+1, 15+8+2+1, 15+8+4+1, 15+8+4+2+1, 15+8+5+2+1, 15+8+5+4+1, 15+8+5+4+2+1, 15+8+7+6+2+1, 15+8+7+6+4+1, 15+8+7+ 6+4+2+1, 15+8+7+6+5+2+1, 15+8+7+6+5+4+1, 15+8+7+ 6+5+4+2+1, 15+10+2+1, 15+10+4+1, 15+10+4+2+1, 15+10+5+2+1, 15+10+5+4+1, 15+10+5+4+2+1, 15+10+8+ 2+1, 15+10+8+4+1, 15+10+8+4+2+1, 15+10+8+5+2+1, 15+10+8+5+4+1, 15+10+8+5+4+2+1, 15+10+8+7+6+2+1, 15+10+8+7+6+4+1, 15+10+8+7+6+4+2+1, 15+10+8+7+6+ 5+2+1, 15+10+8+7+6+5+4+1, 15+10+8+7+6+5+4+2+1, 16+15+2+1, 16+15+4+1, 16+15+4+2+1, 16+15+5+2+1, 16+15+5+4+1, 16+15+5+4+2+1, 16+15+8+2+1, 16+15+8+ 4+1, 16+15+8+4+2+1, 16+15+8+5+2+1, 16+15+8+5+4+1, 16+15+8+5+4+2+1, 16+15+8+7+6+2+1, 16+15+8+7+6+4+ 1, 16+15+8+7+6+4+2+1, 16+15+8+7+6+5+2+1, 16+15+8+ 7+6+5+4+1, 16+15+8+7+6+5+4+2+1, 16+15+10+2+1, 16+15+10+4+1, 16+15+10+4+2+1, 16+15+10+5+2+1, 16+15+10+5+4+1, 16+15+10+5+4+2+1, 16+15+10+8+2+1, 16+15+10+8+4+1, 16+15+10+8+4+2+1, 16+15+10+8+5+ 2+1, 16+15+10+8+5+4+1, 16+15+10+8+5+4+2+1, 16+15+ 10+8+7+6+2+1, 16+15+10+8+7+6+4+1, 16+15+10+8+7+ 6+4+2+1, 16+15+10+8+7+6+5+2+1, 16+15+10+8+7+6+5+ 4+1, 16+15+10+8+7+6+5+4+2+1, 17+2+1, 17+4+1, 17+4+ 2+1, 17+5+2+1, 17+5+4+1, 17+5+4+2+1, 17+8+2+1, 17+8+4+1, 17+8+4+2+1, 17+8+5+2+1, 17+8+5+4+1, 17+8+5+4+2+1, 17+8+7+6+2+1, 17+8+7+6+4+1, 17+8+7+ 6+4+2+1, 17+8+7+6+5+2+1, 17+8+7+6+5+4+1, 17+8+7+ 6+5+4+2+1, 17+10+2+1, 17+10+4+1, 17+10+4+2+1, 17+10+5+2+1, 17+10+5+4+1, 17+10+5+4+2+1, 17+10+8+ 2+1, 17+10+8+4+1, 17+10+8+4+2+1, 17+10+8+5+2+1, 17+10+8+5+4+1, 17+10+8+5+4+2+1, 17+10+8+7+6+2+1, 17+10+8+7+6+4+1, 17+10+8+7+6+4+2+1, 17+10+8+7+6+ 5+2+1, 17+10+8+7+6+5+4+1, 17+10+8+7+6+5+4+2+1, 17+16+15+2+1, 17+16+15+4+1, 17+16+15+4+2+1, 17+16+15+5+2+1, 17+16+15+5+4+1, 17+16+15+5+4+2+1, 17+16+15+8+2+1, 17+16+15+8+4+1, 17+16+15+8+4+2+1, 17+16+15+8+5+2+1, 17+16+15+8+5+4+1, 17+16+15+8+ 5+4+2+1, 17+16+15+8+7+6+2+1, 17+16+15+8+7+6+4+1, 17+16+15+8+7+6+4+2+1, 17+16+15+8+7+6+5+2+1, 17+16+15+8+7+6+5+4+1, 17+16+15+8+7+6+5+4+2+1, 17+16+15+10+2+1, 17+16+15+10+4+1, 17+16+15+10+4+ 2+1, 17+16+15+10+5+2+1, 17+16+15+10+5+4+1, 17+16+ 15+10+5+4+2+1, 17+16+15+10+8+2+1, 17+16+15+10+8+ 4+1, 17+16+15+10+8+4+2+1, 17+16+15+10+8+5+2+1, 17+16+15+10+8+5+4+1, 17+16+15+10+8+5+4+2+1, 17+16+15+10+8+7+6+2+1, 17+16+15+10+8+7+6+4+1, 17+16+15+10+8+7+6+4+2+1, 17+16+15+10+8+7+6+5+2+ 1, 17+16+15+10+8+7+6+5+4+1, 17+16+15+10+8+7+6+5+ 4+2+1, 18+17+2+1, 18+17+4+1, 18+17+4+2+1, 18+17+5+ 2+1, 18+17+5+4+1, 18+17+5+4+2+1, 18+17+8+2+1, 18+17+8+4+1, 18+17+8+4+2+1, 18+17+8+5+2+1, 18+17+ 8+5+4+1, 18+17+8+5+4+2+1, 18+17+8+7+6+2+1, 18+17+ 8+7+6+4+1, 18+17+8+7+6+4+2+1, 18+17+8+7+6+5+2+1, 18+17+8+7+6+5+4+1, 18+17+8+7+6+5+4+2+1, 18+17+ 10+2+1, 18+17+10+4+1, 18+17+10+4+2+1, 18+17+10+5+ 2+1, 18+17+10+5+4+1, 18+17+10+5+4+2+1, 18+17+10+ 8+2+1, 18+17+10+8+4+1, 18+17+10+8+4+2+1, 18+17+ 10+8+5+2+1, 18+17+10+8+5+4+1, 18+17+10+8+5+4+2+1, 18+17+10+8+7+6+2+1, 18+17+10+8+7+6+4+1, 18+17+ 10+8+7+6+4+2+1, 18+17+10+8+7+6+5+2+1, 18+17+10+ 8+7+6+5+4+1, 18+17+10+8+7+6+5+4+2+1, 18+17+16+ 15+2+1, 18+17+16+15+4+1, 18+17+16+15+4+2+1, 18+17+16+15+5+2+1, 18+17+16+15+5+4+1, 18+17+16+ 15+5+4+2+1, 18+17+16+15+8+2+1, 18+17+16+15+8+4+1, 18+17+16+15+8+4+2+1, 18+17+16+15+8+5+2+1, 18+17+ 16+15+8+5+4+1, 18+17+16+15+8+5+4+2+1, 18+17+16+ 15+8+7+6+2+1, 18+17+16+15+8+7+6+4+1, 18+17+16+ 15+8+7+6+4+2+1, 18+17+16+15+8+7+6+5+2+1, 18+17+ 16+15+8+7+6+5+4+1, 18+17+16+15+8+7+6+5+4+2+1, 18+17+16+15+10+2+1, 18+17+16+15+10+4+1, 18+17+ 16+15+10+4+2+1, 18+17+16+15+10+5+2+1, 18+17+16+ 15+10+5+4+1, 18+17+16+15+10+5+4+2+1, 18+17+16+ 15+10+8+2+1, 18+17+16+15+10+8+4+1, 18+17+16+15+ 10+8+4+2+1, 18+17+16+15+10+8+5+2+1, 18+17+16+15+ 10+8+5+4+1, 18+17+16+15+10+8+5+4+2+1, 18+17+16+ 15+10+8+7+6+2+1, 18+17+16+15+10+8+7+6+4+1, 18+17+16+15+10+8+7+6+4+2+1, 18+17+16+15+10+8+7+ 6+5+2+1, 18+17+16+15+10+8+7+6+5+4+1, 18+17+16+ 15+10+8+7+6+5+4+2+1, 19+18+17+2+1, 19+18+17+4+1, 19+18+17+4+2+1, 19+18+17+5+2+1, 19+18+17+5+4+1, 19+18+17+5+4+2+1, 19+18+17+8+2+1, 19+18+17+8+4+1, 19+18+17+8+4+2+1, 19+18+17+8+5+2+1, 19+18+17+8+ 5+4+1, 19+18+17+8+5+4+2+1, 19+18+17+8+7+6+2+1, 19+18+17+8+7+6+4+1, 19+18+17+8+7+6+4+2+1, 19+18+ 17+8+7+6+5+2+1, 19+18+17+8+7+6+5+4+1, 19+18+17+ 8+7+6+5+4+2+1, 19+18+17+10+2+1, 19+18+17+10+4+1, 19+18+17+10+4+2+1, 19+18+17+10+5+2+1, 19+18+17+ 10+5+4+1, 19+18+17+10+5+4+2+1, 19+18+17+10+8+2+1, 19+18+17+10+8+4+1, 19+18+17+10+8+4+2+1, 19+18+ 17+10+8+5+2+1, 19+18+17+10+8+5+4+1, 19+18+17+10+ 8+5+4+2+1, 19+18+17+10+8+7+6+2+1, 19+18+17+10+8+ 7+6+4+1, 19+18+17+10+8+7+6+4+2+1, 19+18+17+10+8+ 7+6+5+2+1, 19+18+17+10+8+7+6+5+4+1, 19+18+17+10+ 8+7+6+5+4+2+1, 19+18+17+16+15+2+1, 19+18+17+16+ 15+4+1, 19+18+17+16+15+4+2+1, 19+18+17+16+15+5+ 2+1, 19+18+17+16+15+5+4+1, 19+18+17+16+15+5+4+2+ 1, 19+18+17+16+15+8+2+1, 19+18+17+16+15+8+4+1, 19+18+17+16+15+8+4+2+1, 19+18+17+16+15+8+5+2+1, 19+18+17+16+15+8+5+4+1, 19+18+17+16+15+8+5+4+2+ 1, 19+18+17+16+15+8+7+6+2+1, 19+18+17+16+15+8+7+ 6+4+1, 19+18+17+16+15+8+7+6+4+2+1, 19+18+17+16+ 15+8+7+6+5+2+1, 19+18+17+16+15+8+7+6+5+4+1, 19+18+17+16+15+8+7+6+5+4+2+1, 19+18+17+16+15+ 10+2+1, 19+18+17+16+15+10+4+1, 19+18+17+16+15+ 10+4+2+1, 19+18+17+16+15+10+5+2+1, 19+18+17+16+ 15+10+5+4+1, 19+18+17+16+15+10+5+4+2+1, 19+18+ 17+16+15+10+8+2+1, 19+18+17+16+15+10+8+4+1, 19+18+17+16+15+10+8+4+2+1, 19+18+17+16+15+10+8+ 5+2+1, 19+18+17+16+15+10+8+5+4+1, 19+18+17+16+ 15+10+8+5+4+2+1, 19+18+17+16+15+10+8+7+6+2+1, 19+18+17+16+15+10+8+7+6+4+1, 19+18+17+16+15+10+ 8+7+6+4+2+1, 19+18+17+16+15+10+8+7+6+5+2+1, 19+18+17+16+15+10+8+7+6+5+4+1, 19+18+17+16+15+ 10+8+7+6+5+4+2+1, 20+18+17+2+1, 20+18+17+4+1, 20+18+17+4+2+1, 20+18+17+5+2+1, 20+18+17+5+4+1,

20+18+17+5+4+2+1, 20+18+17+8+2+1, 20+18+17+8+4+1, 20+18+17+8+4+2+1, 20+18+17+8+5+2+1, 20+18+17+8+5+4+1, 20+18+17+8+5+4+2+1, 20+18+17+8+7+6+2+1, 20+18+17+8+7+6+4+1, 20+18+17+8+7+6+4+2+1, 20+18+17+8+7+6+5+2+1, 20+18+17+8+7+6+5+4+1, 20+18+17+8+7+6+5+4+2+1, 20+18+17+10+2+1, 20+18+17+10+4+1, 20+18+17+10+4+2+1, 20+18+17+10+5+2+1, 20+18+17+10+5+4+1, 20+18+17+10+5+4+2+1, 20+18+17+10+8+2+1, 20+18+17+10+8+4+1, 20+18+17+10+8+4+2+1, 20+18+17+10+8+5+2+1, 20+18+17+10+8+5+4+1, 20+18+17+10+8+5+4+2+1, 20+18+17+10+8+7+6+2+1, 20+18+17+10+8+7+6+4+1, 20+18+17+10+8+7+6+4+2+1, 20+18+17+10+8+7+6+5+2+1, 20+18+17+10+8+7+6+5+4+1, 20+18+17+10+8+7+6+5+4+2+1, 20+18+17+16+15+2+1, 20+18+17+16+15+4+1, 20+18+17+16+15+4+2+1, 20+18+17+16+15+5+2+1, 20+18+17+16+15+5+4+1, 20+18+17+16+15+5+4+2+1, 20+18+17+16+15+8+2+1, 20+18+17+16+15+8+4+1, 20+18+17+16+15+8+4+2+1, 20+18+17+16+15+8+5+2+1, 20+18+17+16+15+8+5+4+1, 20+18+17+16+15+8+5+4+2+1, 20+18+17+16+15+8+7+6+2+1, 20+18+17+16+15+8+7+6+4+1, 20+18+17+16+15+8+7+6+4+2+1, 20+18+17+16+15+8+7+6+5+2+1, 20+18+17+16+15+8+7+6+5+4+1, 20+18+17+16+15+8+7+6+5+4+2+1, 20+18+17+16+15+10+2+1, 20+18+17+16+15+10+4+1, 20+18+17+16+15+10+4+2+1, 20+18+17+16+15+10+5+2+1, 20+18+17+16+15+10+5+4+1, 20+18+17+16+15+10+5+4+2+1, 20+18+17+16+15+10+8+2+1, 20+18+17+16+15+10+8+4+1, 20+18+17+16+15+10+8+4+2+1, 20+18+17+16+15+10+8+5+2+1, 20+18+17+16+15+10+8+5+4+1, 20+18+17+16+15+10+8+5+4+2+1, 20+18+17+16+15+10+8+7+6+2+1, 20+18+17+16+15+10+8+7+6+4+1, 20+18+17+16+15+10+8+7+6+4+2+1, 20+18+17+16+15+10+8+7+6+5+2+1, 20+18+17+16+15+10+8+7+6+5+4+1, 20+18+17+16+15+10+8+7+6+5+4+2+1, 20+19+18+17+2+1, 20+19+18+17+4+1, 20+19+18+17+4+2+1, 20+19+18+17+5+2+1, 20+19+18+17+5+4+1, 20+19+18+17+5+4+2+1, 20+19+18+17+8+2+1, 20+19+18+17+8+4+1, 20+19+18+17+8+4+2+1, 20+19+18+17+8+5+2+1, 20+19+18+17+8+5+4+1, 20+19+18+17+8+5+4+2+1, 20+19+18+17+8+7+6+2+1, 20+19+18+17+8+7+6+4+1, 20+19+18+17+8+7+6+4+2+1, 20+19+18+17+8+7+6+5+2+1, 20+19+18+17+8+7+6+5+4+1, 20+19+18+17+8+7+6+5+4+2+1, 20+19+18+17+10+2+1, 20+19+18+17+10+4+1, 20+19+18+17+10+4+2+1, 20+19+18+17+10+5+2+1, 20+19+18+17+10+5+4+1, 20+19+18+17+10+5+4+2+1, 20+19+18+17+10+8+2+1, 20+19+18+17+10+8+4+1, 20+19+18+17+10+8+4+2+1, 20+19+18+17+10+8+5+2+1, 20+19+18+17+10+8+5+4+1, 20+19+18+17+10+8+5+4+2+1, 20+19+18+17+10+8+7+6+2+1, 20+19+18+17+10+8+7+6+4+1, 20+19+18+17+10+8+7+6+4+2+1, 20+19+18+17+10+8+7+6+5+2+1, 20+19+18+17+10+8+7+6+5+4+1, 20+19+18+17+10+8+7+6+5+4+2+1, 20+19+18+17+16+15+2+1, 20+19+18+17+16+15+4+1, 20+19+18+17+16+15+4+2+1, 20+19+18+17+16+15+5+2+1, 20+19+18+17+16+15+5+4+1, 20+19+18+17+16+15+5+4+2+1, 20+19+18+17+16+15+8+2+1, 20+19+18+17+16+15+8+4+1, 20+19+18+17+16+15+8+4+2+1, 20+19+18+17+16+15+8+5+2+1, 20+19+18+17+16+15+8+5+4+1, 20+19+18+17+16+15+8+5+4+2+1, 20+19+18+17+16+15+8+7+6+2+1, 20+19+18+17+16+15+8+7+6+4+1, 20+19+18+17+16+15+8+7+6+4+2+1, 20+19+18+17+16+15+8+7+6+5+2+1, 20+19+18+17+16+15+8+7+6+5+4+1, 20+19+18+17+16+15+8+7+6+5+4+2+1, 20+19+18+17+16+15+10+2+1, 20+19+18+17+16+15+10+4+1, 20+19+18+17+16+15+10+4+2+1, 20+19+18+17+16+15+10+5+2+1, 20+19+18+17+16+15+10+5+4+1, 20+19+18+17+16+15+10+5+4+2+1, 20+19+18+17+16+15+10+8+2+1, 20+19+18+17+16+15+10+8+4+1, 20+19+18+17+16+15+10+8+4+2+1, 20+19+18+17+16+15+10+8+5+2+1, 20+19+18+17+16+15+10+8+5+4+1, 20+19+18+17+16+15+10+8+5+4+2+1, 20+19+18+17+16+15+10+8+7+6+2+1, 20+19+18+17+16+15+10+8+7+6+4+1, 20+19+18+17+16+15+10+8+7+6+4+2+1, 20+19+18+17+16+15+10+8+7+6+5+2+1, 20+19+18+17+16+15+10+8+7+6+5+4+1, 20+19+18+17+16+15+10+8+7+6+5+4+2+1, 21+18+17+2+1, 21+18+17+4+1, 21+18+17+4+2+1, 21+18+17+5+2+1, 21+18+17+5+4+1, 21+18+17+5+4+2+1, 21+18+17+8+2+1, 21+18+17+8+4+1, 21+18+17+8+4+2+1, 21+18+17+8+5+2+1, 21+18+17+8+5+4+1, 21+18+17+8+5+4+2+1, 21+18+17+8+7+6+2+1, 21+18+17+8+7+6+4+1, 21+18+17+8+7+6+4+2+1, 21+18+17+8+7+6+5+2+1, 21+18+17+8+7+6+5+4+1, 21+18+17+8+7+6+5+4+2+1, 21+18+17+10+2+1, 21+18+17+10+4+1, 21+18+17+10+4+2+1, 21+18+17+10+5+2+1, 21+18+17+10+5+4+1, 21+18+17+10+5+4+2+1, 21+18+17+10+8+2+1, 21+18+17+10+8+4+1, 21+18+17+10+8+4+2+1, 21+18+17+10+8+5+2+1, 21+18+17+10+8+5+4+1, 21+18+17+10+8+5+4+2+1, 21+18+17+10+8+7+6+2+1, 21+18+17+10+8+7+6+4+1, 21+18+17+10+8+7+6+4+2+1, 21+18+17+10+8+7+6+5+2+1, 21+18+17+10+8+7+6+5+4+1, 21+18+17+10+8+7+6+5+4+2+1, 21+18+17+16+15+2+1, 21+18+17+16+15+4+1, 21+18+17+16+15+4+2+1, 21+18+17+16+15+5+2+1, 21+18+17+16+15+5+4+1, 21+18+17+16+15+5+4+2+1, 21+18+17+16+15+8+2+1, 21+18+17+16+15+8+4+1, 21+18+17+16+15+8+4+2+1, 21+18+17+16+15+8+5+2+1, 21+18+17+16+15+8+5+4+1, 21+18+17+16+15+8+5+4+2+1, 21+18+17+16+15+8+7+6+2+1, 21+18+17+16+15+8+7+6+4+1, 21+18+17+16+15+8+7+6+4+2+1, 21+18+17+16+15+8+7+6+5+2+1, 21+18+17+16+15+8+7+6+5+4+1, 21+18+17+16+15+8+7+6+5+4+2+1, 21+18+17+16+15+10+2+1, 21+18+17+16+15+10+4+1, 21+18+17+16+15+10+4+2+1, 21+18+17+16+15+10+5+2+1, 21+18+17+16+15+10+5+4+1, 21+18+17+16+15+10+5+4+2+1, 21+18+17+16+15+10+8+2+1, 21+18+17+16+15+10+8+4+1, 21+18+17+16+15+10+8+4+2+1, 21+18+17+16+15+10+8+5+2+1, 21+18+17+16+15+10+8+5+4+1, 21+18+17+16+15+10+8+5+4+2+1, 21+18+17+16+15+10+8+7+6+2+1, 21+18+17+16+15+10+8+7+6+4+1, 21+18+17+16+15+10+8+7+6+4+2+1, 21+18+17+16+15+10+8+7+6+5+2+1, 21+18+17+16+15+10+8+7+6+5+4+1, 21+18+17+16+15+10+8+7+6+5+4+2+1, 21+19+18+17+2+1, 21+19+18+17+4+1, 21+19+18+17+4+2+1, 21+19+18+17+5+2+1, 21+19+18+17+5+4+1, 21+19+18+17+5+4+2+1, 21+19+18+17+8+2+1, 21+19+18+17+8+4+1, 21+19+18+17+8+4+2+1, 21+19+18+17+8+5+2+1, 21+19+18+17+8+5+4+1, 21+19+18+17+8+5+4+2+1, 21+19+18+17+8+7+6+2+1, 21+19+18+17+8+7+6+4+1, 21+19+18+17+8+7+6+4+2+1, 21+19+18+17+8+7+6+5+2+1, 21+19+18+17+8+7+6+5+4+1, 21+19+18+17+8+7+6+5+4+2+1, 21+19+18+17+10+2+1, 21+19+18+17+10+4+1, 21+19+18+17+10+4+2+1, 21+19+18+17+10+5+2+1, 21+19+18+17+10+5+4+1, 21+19+18+17+10+5+4+2+1, 21+19+18+17+10+8+2+1, 21+19+18+17+10+8+4+1, 21+19+18+17+10+8+4+2+1, 21+19+18+17+10+8+5+2+1, 21+19+18+17+10+8+5+4+1, 21+19+18+17+10+8+5+4+2+1, 21+19+18+17+10+8+7+6+2+1, 21+19+18+17+10+8+7+6+4+1, 21+19+18+17+10+8+7+6+4+2+1, 21+19+18+17+10+8+7+6+5+2+1, 21+19+18+17+10+8+7+6+5+4+1, 21+19+18+17+10+8+7+6+5+4+2+1, 21+19+18+17+16+15+2+1, 21+19+18+17+16+15+4+1, 21+19+18+17+16+15+4+2+1, 21+19+18+17+16+15+5+2+1, 21+19+18+17+16+15+5+4+1, 21+19+18+17+16+15+5+4+2+1, 21+19+18+17+16+15+8+2+1, 21+19+18+17+16+15+8+4+1, 21+19+18+17+16+15+8+4+2+1, 21+19+18+17+16+15+8+5+2+1, 21+19+18+17+16+15+8+5+4+1, 21+19+18+17+16+15+8+5+4+2+1, 21+19+18+17+16+15+8+7+6+2+1, 21+19+18+17+16+15+8+7+6+4+1, 21+19+

18+17+16+15+8+7+6+4+2+1, 21+19+18+17+16+15+8+7+ 6+5+2+1, 21+19+18+17+16+15+8+7+6+5+4+1, 21+19+ 18+17+16+15+8+7+6+5+4+2+1, 21+19+18+17+16+15+ 10+2+1, 21+19+18+17+16+15+10+4+1, 21+19+18+17+ 16+15+10+4+2+1, 21+19+18+17+16+15+10+5+2+1, 21+19+18+17+16+15+10+5+4+1, 21+19+18+17+16+15+ 10+5+4+2+1, 21+19+18+17+16+15+10+8+2+1, 21+19+ 18+17+16+15+10+8+4+1, 21+19+18+17+16+15+10+8+4+ 2+1, 21+19+18+17+16+15+10+8+5+2+1, 21+19+18+17+ 16+15+10+8+5+4+1, 21+19+18+17+16+15+10+8+5+4+2+ 1, 21+19+18+17+16+15+10+8+7+6+2+1, 21+19+18+17+ 16+15+10+8+7+6+4+1, 21+19+18+17+16+15+10+8+7+6+ 4+2+1, 21+19+18+17+16+15+10+8+7+6+5+2+1, 21+19+ 18+17+16+15+10+8+7+6+5+4+1, 21+19+18+17+16+15+ 10+8+7+6+5+4+2+1, 22+2+1, 22+4+1, 22+4+2+1, 22+5+ 2+1, 22+5+4+1, 22+5+4+2+1, 22+8+2+1, 22+8+4+1, 22+8+4+2+1, 22+8+5+2+1, 22+8+5+4+1, 22+8+5+4+2+1, 22+8+7+6+2+1, 22+8+7+6+4+1, 22+8+7+6+4+2+1, 22+8+ 7+6+5+2+1, 22+8+7+6+5+4+1, 22+8+7+6+5+4+2+1, 22+10+2+1, 22+10+4+1, 22+10+4+2+1, 22+10+5+2+1, 22+10+5+4+1, 22+10+5+4+2+1, 22+10+8+2+1, 22+10+8+ 4+1, 22+10+8+4+2+1, 22+10+8+5+2+1, 22+10+8+5+4+1, 22+10+8+5+4+2+1, 22+10+8+7+6+2+1, 22+10+8+7+6+4+ 1, 22+10+8+7+6+4+2+1, 22+10+8+7+6+5+2+1, 22+10+8+ 7+6+5+4+1, 22+10+8+7+6+5+4+2+1, 22+16+15+2+1, 22+16+15+4+1, 22+16+15+4+2+1, 22+16+15+5+2+1, 22+16+15+5+4+1, 22+16+15+5+4+2+1, 22+16+15+8+2+1, 22+16+15+8+4+1, 22+16+15+8+4+2+1, 22+16+15+8+5+ 2+1, 22+16+15+8+5+4+1, 22+16+15+8+5+4+2+1, 22+16+ 15+8+7+6+2+1, 22+16+15+8+7+6+4+1, 22+16+15+8+7+ 6+4+2+1, 22+16+15+8+7+6+5+2+1, 22+16+15+8+7+6+5+ 4+1, 22+16+15+8+7+6+5+4+2+1, 22+16+15+10+2+1, 22+16+15+10+4+1, 22+16+15+10+4+2+1, 22+16+15+10+ 5+2+1, 22+16+15+10+5+4+1, 22+16+15+10+5+4+2+1, 22+16+15+10+8+2+1, 22+16+15+10+8+4+1, 22+16+15+ 10+8+4+2+1, 22+16+15+10+8+5+2+1, 22+16+15+10+8+ 5+4+1, 22+16+15+10+8+5+4+2+1, 22+16+15+10+8+7+6+ 2+1, 22+16+15+10+8+7+6+4+1, 22+16+15+10+8+7+6+4+ 2+1, 22+16+15+10+8+7+6+5+2+1, 22+16+15+10+8+7+6+ 5+4+1, 22+16+15+10+8+7+6+5+4+2+1, 22+18+17+2+1, 22+18+17+4+1, 22+18+17+4+2+1, 22+18+17+5+2+1, 22+18+17+5+4+1, 22+18+17+5+4+2+1, 22+18+17+8+2+1, 22+18+17+8+4+1, 22+18+17+8+4+2+1, 22+18+17+8+5+ 2+1, 22+18+17+8+5+4+1, 22+18+17+8+5+4+2+1, 22+18+ 17+8+7+6+2+1, 22+18+17+8+7+6+4+1, 22+18+17+8+7+ 6+4+2+1, 22+18+17+8+7+6+5+2+1, 22+18+17+8+7+6+5+ 4+1, 22+18+17+8+7+6+5+4+2+1, 22+18+17+10+2+1, 22+18+17+10+4+1, 22+18+17+10+4+2+1, 22+18+17+10+ 5+2+1, 22+18+17+10+5+4+1, 22+18+17+10+5+4+2+1, 22+18+17+10+8+2+1, 22+18+17+10+8+4+1, 22+18+17+ 10+8+4+2+1, 22+18+17+10+8+5+2+1, 22+18+17+10+8+ 5+4+1, 22+18+17+10+8+5+4+2+1, 22+18+17+10+8+7+6+ 2+1, 22+18+17+10+8+7+6+4+1, 22+18+17+10+8+7+6+4+ 2+1, 22+18+17+10+8+7+6+5+2+1, 22+18+17+10+8+7+6+ 5+4+1, 22+18+17+10+8+7+6+5+4+2+1, 22+18+17+16+ 15+2+1, 22+18+17+16+15+4+1, 22+18+17+16+15+4+2+1, 22+18+17+16+15+5+2+1, 22+18+17+16+15+5+4+1, 22+18+17+16+15+5+4+2+1, 22+18+17+16+15+8+2+1, 22+18+17+16+15+8+4+1, 22+18+17+16+15+8+4+2+1, 22+18+17+16+15+8+5+2+1, 22+18+17+16+15+8+5+4+1, 22+18+17+16+15+8+5+4+2+1, 22+18+17+16+15+8+7+6+ 2+1, 22+18+17+16+15+8+7+6+4+1, 22+18+17+16+15+8+ 7+6+4+2+1, 22+18+17+16+15+8+7+6+5+2+1, 22+18+17+ 16+15+8+7+6+5+4+1, 22+18+17+16+15+8+7+6+5+4+2+ 1, 22+18+17+16+15+10+2+1, 22+18+17+16+15+10+4+1, 22+18+17+16+15+10+4+2+1, 22+18+17+16+15+10+5+2+ 1, 22+18+17+16+15+10+5+4+1, 22+18+17+16+15+10+5+ 4+2+1, 22+18+17+16+15+10+8+2+1, 22+18+17+16+15+ 10+8+4+1, 22+18+17+16+15+10+8+4+2+1, 22+18+17+ 16+15+10+8+5+2+1, 22+18+17+16+15+10+8+5+4+1, 22+18+17+16+15+10+8+5+4+2+1, 22+18+17+16+15+10+ 8+7+6+2+1, 22+18+17+16+15+10+8+7+6+4+1, 22+18+ 17+16+15+10+8+7+6+4+2+1, 22+18+17+16+15+10+8+7+ 6+5+2+1, 22+18+17+16+15+10+8+7+6+5+4+1, 22+18+ 17+16+15+10+8+7+6+5+4+2+1, 22+21+18+17+2+1, 22+21+18+17+4+1, 22+21+18+17+4+2+1, 22+21+18+17+ 5+2+1, 22+21+18+17+5+4+1, 22+21+18+17+5+4+2+1, 22+21+18+17+8+2+1, 22+21+18+17+8+4+1, 22+21+18+ 17+8+4+2+1, 22+21+18+17+8+5+2+1, 22+21+18+17+8+ 5+4+1, 22+21+18+17+8+5+4+2+1, 22+21+18+17+8+7+6+ 2+1, 22+21+18+17+8+7+6+4+1, 22+21+18+17+8+7+6+4+ 2+1, 22+21+18+17+8+7+6+5+2+1, 22+21+18+17+8+7+6+ 5+4+1, 22+21+18+17+8+7+6+5+4+2+1, 22+21+18+17+ 10+2+1, 22+21+18+17+10+4+1, 22+21+18+17+10+4+2+1, 22+21+18+17+10+5+2+1, 22+21+18+17+10+5+4+1, 22+21+18+17+10+5+4+2+1, 22+21+18+17+10+8+2+1, 22+21+18+17+10+8+4+1, 22+21+18+17+10+8+4+2+1, 22+21+18+17+10+8+5+2+1, 22+21+18+17+10+8+5+4+1, 22+21+18+17+10+8+5+4+2+1, 22+21+18+17+10+8+7+6+ 2+1, 22+21+18+17+10+8+7+6+4+1, 22+21+18+17+10+8+ 7+6+4+2+1, 22+21+18+17+10+8+7+6+5+2+1, 22+21+18+ 17+10+8+7+6+5+4+1, 22+21+18+17+10+8+7+6+5+4+2+ 1, 22+21+18+17+16+15+2+1, 22+21+18+17+16+15+4+1, 22+21+18+17+16+15+4+2+1, 22+21+18+17+16+15+5+2+ 1, 22+21+18+17+16+15+5+4+1, 22+21+18+17+16+15+5+ 4+2+1, 22+21+18+17+16+15+8+2+1, 22+21+18+17+16+ 15+8+4+1, 22+21+18+17+16+15+8+4+2+1, 22+21+18+ 17+16+15+8+5+2+1, 22+21+18+17+16+15+8+5+4+1, 22+21+18+17+16+15+8+5+4+2+1, 22+21+18+17+16+15+ 8+7+6+2+1, 22+21+18+17+16+15+8+7+6+4+1, 22+21+ 18+17+16+15+8+7+6+4+2+1, 22+21+18+17+16+15+8+7+ 6+5+2+1, 22+21+18+17+16+15+8+7+6+5+4+1, 22+21+ 18+17+16+15+8+7+6+5+4+2+1, 22+21+18+17+16+15+ 10+2+1, 22+21+18+17+16+15+10+4+1, 22+21+18+17+ 16+15+10+4+2+1, 22+21+18+17+16+15+10+5+2+1, 22+21+18+17+16+15+10+5+4+1, 22+21+18+17+16+15+ 10+5+4+2+1, 22+21+18+17+16+15+10+8+2+1, 22+21+ 18+17+16+15+10+8+4+1, 22+21+18+17+16+15+10+8+4+ 2+1, 22+21+18+17+16+15+10+8+5+2+1, 22+21+18+17+ 16+15+10+8+5+4+1, 22+21+18+17+16+15+10+8+5+4+2+ 1, 22+21+18+17+16+15+10+8+7+6+2+1, 22+21+18+17+ 16+15+10+8+7+6+4+1, 22+21+18+17+16+15+10+8+7+6+ 4+2+1, 22+21+18+17+16+15+10+8+7+6+5+2+1, 22+21+ 18+17+16+15+10+8+7+6+5+4+1, 22+21+18+17+16+15+ 10+8+7+6+5+4+2+1, 22+21+19+18+17+2+1, 22+21+19+ 18+17+4+1, 22+21+19+18+17+4+2+1, 22+21+19+18+17+ 5+2+1, 22+21+19+18+17+5+4+1, 22+21+19+18+17+5+4+ 2+1, 22+21+19+18+17+8+2+1, 22+21+19+18+17+8+4+1, 22+21+19+18+17+8+4+2+1, 22+21+19+18+17+8+5+2+1, 22+21+19+18+17+8+5+4+1, 22+21+19+18+17+8+5+4+2+ 1, 22+21+19+18+17+8+7+6+2+1, 22+21+19+18+17+8+7+ 6+4+1, 22+21+19+18+17+8+7+6+4+2+1, 22+21+19+18+ 17+8+7+6+5+2+1, 22+21+19+18+17+8+7+6+5+4+1, 22+21+19+18+17+8+7+6+5+4+2+1, 22+21+19+18+17+ 10+2+1, 22+21+19+18+17+10+4+1, 22+21+19+18+17+ 10+4+2+1, 22+21+19+18+17+10+5+2+1, 22+21+19+18+ 17+10+5+4+1, 22+21+19+18+17+10+5+4+2+1, 22+21+ 19+18+17+10+8+2+1, 22+21+19+18+17+10+8+4+1, 22+21+19+18+17+10+8+4+2+1, 22+21+19+18+17+10+8+ 5+2+1, 22+21+19+18+17+10+8+5+4+1, 22+21+19+18+ 17+10+8+5+4+2+1, 22+21+19+18+17+10+8+7+6+2+1, 22+21+19+18+17+10+8+7+6+4+1, 22+21+19+18+17+10+ 8+7+6+4+2+1, 22+21+19+18+17+10+8+7+6+5+2+1, 22+21+19+18+17+10+8+7+6+5+4+1, 22+21+19+18+17+

10+8+7+6+5+4+2+1, 22+21+19+18+17+16+15+2+1, 22+21+19+18+17+16+15+4+1, 22+21+19+18+17+16+15+4+2+1, 22+21+19+18+17+16+15+5+2+1, 22+21+19+18+17+16+15+5+4+1, 22+21+19+18+17+16+15+5+4+2+1, 22+21+19+18+17+16+15+8+2+1, 22+21+19+18+17+16+15+8+4+1, 22+21+19+18+17+16+15+8+4+2+1, 22+21+19+18+17+16+15+8+5+2+1, 22+21+19+18+17+16+15+8+5+4+1, 22+21+19+18+17+16+15+8+5+4+2+1, 22+21+19+18+17+16+15+8+7+6+2+1, 22+21+19+18+17+16+15+8+7+6+4+1, 22+21+19+18+17+16+15+8+7+6+4+2+1, 22+21+19+18+17+16+15+8+7+6+5+2+1, 22+21+19+18+17+16+15+8+7+6+5+4+1, 22+21+19+18+17+16+15+8+7+6+5+4+2+1, 22+21+19+18+17+16+15+10+2+1, 22+21+19+18+17+16+15+10+4+1, 22+21+19+18+17+16+15+10+4+2+1, 22+21+19+18+17+16+15+10+5+2+1, 22+21+19+18+17+16+15+10+5+4+1, 22+21+19+18+17+16+15+10+5+4+2+1, 22+21+19+18+17+16+15+10+8+2+1, 22+21+19+18+17+16+15+10+8+4+1, 22+21+19+18+17+16+15+10+8+4+2+1, 22+21+19+18+17+16+15+10+8+5+2+1, 22+21+19+18+17+16+15+10+8+5+4+1, 22+21+19+18+17+16+15+10+8+5+4+2+1, 22+21+19+18+17+16+15+10+8+7+6+2+1, 22+21+19+18+17+16+15+10+8+7+6+4+1, 22+21+19+18+17+16+15+10+8+7+6+4+2+1, 22+21+19+18+17+16+15+10+8+7+6+5+2+1, 22+21+19+18+17+16+15+10+8+7+6+5+4+1, 22+21+19+18+17+16+15+10+8+7+6+5+4+2+1, 23+2+1, 23+4+1, 23+4+2+1, 23+5+2+1, 23+5+4+1, 23+5+4+2+1, 23+8+2+1, 23+8+4+1, 23+8+4+2+1, 23+8+5+2+1, 23+8+5+4+1, 23+8+5+4+2+1, 23+8+7+6+2+1, 23+8+7+6+4+1, 23+8+7+6+4+2+1, 23+8+7+6+5+2+1, 23+8+7+6+5+4+1, 23+8+7+6+5+4+2+1, 23+10+2+1, 23+10+4+1, 23+10+4+2+1, 23+10+5+2+1, 23+10+5+4+1, 23+10+5+4+2+1, 23+10+8+2+1, 23+10+8+4+1, 23+10+8+4+2+1, 23+10+8+5+2+1, 23+10+8+5+4+1, 23+10+8+5+4+2+1, 23+10+8+7+6+2+1, 23+10+8+7+6+4+1, 23+10+8+7+6+4+2+1, 23+10+8+7+6+5+2+1, 23+10+8+7+6+5+4+1, 23+10+8+7+6+5+4+2+1, 23+16+15+2+1, 23+16+15+4+1, 23+16+15+4+2+1, 23+16+15+5+2+1, 23+16+15+5+4+1, 23+16+15+5+4+2+1, 23+16+15+8+2+1, 23+16+15+8+4+1, 23+16+15+8+4+2+1, 23+16+15+8+5+2+1, 23+16+15+8+5+4+1, 23+16+15+8+5+4+2+1, 23+16+15+8+7+6+2+1, 23+16+15+8+7+6+4+1, 23+16+15+8+7+6+4+2+1, 23+16+15+8+7+6+5+2+1, 23+16+15+8+7+6+5+4+1, 23+16+15+8+7+6+5+4+2+1, 23+16+15+10+2+1, 23+16+15+10+4+1, 23+16+15+10+4+2+1, 23+16+15+10+5+2+1, 23+16+15+10+5+4+1, 23+16+15+10+5+4+2+1, 23+16+15+10+8+2+1, 23+16+15+10+8+4+1, 23+16+15+10+8+4+2+1, 23+16+15+10+8+5+2+1, 23+16+15+10+8+5+4+1, 23+16+15+10+8+5+4+2+1, 23+16+15+10+8+7+6+2+1, 23+16+15+10+8+7+6+4+1, 23+16+15+10+8+7+6+4+2+1, 23+16+15+10+8+7+6+5+2+1, 23+16+15+10+8+7+6+5+4+1, 23+16+15+10+8+7+6+5+4+2+1, 23+18+17+2+1, 23+18+17+4+1, 23+18+17+4+2+1, 23+18+17+5+2+1, 23+18+17+5+4+1, 23+18+17+5+4+2+1, 23+18+17+8+2+1, 23+18+17+8+4+1, 23+18+17+8+4+2+1, 23+18+17+8+5+2+1, 23+18+17+8+5+4+1, 23+18+17+8+5+4+2+1, 23+18+17+8+7+6+2+1, 23+18+17+8+7+6+4+1, 23+18+17+8+7+6+4+2+1, 23+18+17+8+7+6+5+2+1, 23+18+17+8+7+6+5+4+1, 23+18+17+8+7+6+5+4+2+1, 23+18+17+10+2+1, 23+18+17+10+4+1, 23+18+17+10+4+2+1, 23+18+17+10+5+2+1, 23+18+17+10+5+4+1, 23+18+17+10+5+4+2+1, 23+18+17+10+8+2+1, 23+18+17+10+8+4+1, 23+18+17+10+8+4+2+1, 23+18+17+10+8+5+2+1, 23+18+17+10+8+5+4+1, 23+18+17+10+8+5+4+2+1, 23+18+17+10+8+7+6+2+1, 23+18+17+10+8+7+6+4+1, 23+18+17+10+8+7+6+4+2+1, 23+18+17+10+8+7+6+5+2+1, 23+18+17+10+8+7+6+5+4+1, 23+18+17+10+8+7+6+5+4+2+1, 23+18+17+16+15+2+1, 23+18+17+16+15+4+1, 23+18+17+16+15+4+2+1, 23+18+17+16+15+5+2+1, 23+18+17+16+15+5+4+1, 23+18+17+16+15+5+4+2+1, 23+18+17+16+15+8+2+1, 23+18+17+16+15+8+4+1, 23+18+17+16+15+8+4+2+1, 23+18+17+16+15+8+5+2+1, 23+18+17+16+15+8+5+4+1, 23+18+17+16+15+8+5+4+2+1, 23+18+17+16+15+8+7+6+2+1, 23+18+17+16+15+8+7+6+4+1, 23+18+17+16+15+8+7+6+4+2+1, 23+18+17+16+15+8+7+6+5+2+1, 23+18+17+16+15+8+7+6+5+4+1, 23+18+17+16+15+8+7+6+5+4+2+1, 23+18+17+16+15+10+2+1, 23+18+17+16+15+10+4+1, 23+18+17+16+15+10+4+2+1, 23+18+17+16+15+10+5+2+1, 23+18+17+16+15+10+5+4+1, 23+18+17+16+15+10+5+4+2+1, 23+18+17+16+15+10+8+2+1, 23+18+17+16+15+10+8+4+1, 23+18+17+16+15+10+8+4+2+1, 23+18+17+16+15+10+8+5+2+1, 23+18+17+16+15+10+8+5+4+1, 23+18+17+16+15+10+8+5+4+2+1, 23+18+17+16+15+10+8+7+6+2+1, 23+18+17+16+15+10+8+7+6+4+1, 23+18+17+16+15+10+8+7+6+4+2+1, 23+18+17+16+15+10+8+7+6+5+2+1, 23+18+17+16+15+10+8+7+6+5+4+1, 23+18+17+16+15+10+8+7+6+5+4+2+1, 23+21+18+17+2+1, 23+21+18+17+4+1, 23+21+18+17+4+2+1, 23+21+18+17+5+2+1, 23+21+18+17+5+4+1, 23+21+18+17+5+4+2+1, 23+21+18+17+8+2+1, 23+21+18+17+8+4+1, 23+21+18+17+8+4+2+1, 23+21+18+17+8+5+2+1, 23+21+18+17+8+5+4+1, 23+21+18+17+8+5+4+2+1, 23+21+18+17+8+7+6+2+1, 23+21+18+17+8+7+6+4+1, 23+21+18+17+8+7+6+4+2+1, 23+21+18+17+8+7+6+5+2+1, 23+21+18+17+8+7+6+5+4+1, 23+21+18+17+8+7+6+5+4+2+1, 23+21+18+17+10+2+1, 23+21+18+17+10+4+1, 23+21+18+17+10+4+2+1, 23+21+18+17+10+5+2+1, 23+21+18+17+10+5+4+1, 23+21+18+17+10+5+4+2+1, 23+21+18+17+10+8+2+1, 23+21+18+17+10+8+4+1, 23+21+18+17+10+8+4+2+1, 23+21+18+17+10+8+5+2+1, 23+21+18+17+10+8+5+4+1, 23+21+18+17+10+8+5+4+2+1, 23+21+18+17+10+8+7+6+2+1, 23+21+18+17+10+8+7+6+4+1, 23+21+18+17+10+8+7+6+4+2+1, 23+21+18+17+10+8+7+6+5+2+1, 23+21+18+17+10+8+7+6+5+4+1, 23+21+18+17+10+8+7+6+5+4+2+1, 23+21+18+17+16+15+2+1, 23+21+18+17+16+15+4+1, 23+21+18+17+16+15+4+2+1, 23+21+18+17+16+15+5+2+1, 23+21+18+17+16+15+5+4+1, 23+21+18+17+16+15+5+4+2+1, 23+21+18+17+16+15+8+2+1, 23+21+18+17+16+15+8+4+1, 23+21+18+17+16+15+8+4+2+1, 23+21+18+17+16+15+8+5+2+1, 23+21+18+17+16+15+8+5+4+1, 23+21+18+17+16+15+8+5+4+2+1, 23+21+18+17+16+15+8+7+6+2+1, 23+21+18+17+16+15+8+7+6+4+1, 23+21+18+17+16+15+8+7+6+4+2+1, 23+21+18+17+16+15+8+7+6+5+2+1, 23+21+18+17+16+15+8+7+6+5+4+1, 23+21+18+17+16+15+8+7+6+5+4+2+1, 23+21+18+17+16+15+10+2+1, 23+21+18+17+16+15+10+4+1, 23+21+18+17+16+15+10+4+2+1, 23+21+18+17+16+15+10+5+2+1, 23+21+18+17+16+15+10+5+4+1, 23+21+18+17+16+15+10+5+4+2+1, 23+21+18+17+16+15+10+8+2+1, 23+21+18+17+16+15+10+8+4+1, 23+21+18+17+16+15+10+8+4+2+1, 23+21+18+17+16+15+10+8+5+2+1, 23+21+18+17+16+15+10+8+5+4+1, 23+21+18+17+16+15+10+8+5+4+2+1, 23+21+18+17+16+15+10+8+7+6+2+1, 23+21+18+17+16+15+10+8+7+6+4+1, 23+21+18+17+16+15+10+8+7+6+4+2+1, 23+21+18+17+16+15+10+8+7+6+5+2+1, 23+21+18+17+16+15+10+8+7+6+5+4+1, 23+21+18+17+16+15+10+8+7+6+5+4+2+1, 23+21+19+18+17+2+1, 23+21+19+18+17+4+1, 23+21+19+18+17+4+2+1, 23+21+19+18+17+5+2+1, 23+21+19+18+17+5+4+1, 23+21+19+18+17+5+4+2+1, 23+21+19+18+17+8+2+1, 23+21+19+18+17+8+4+1, 23+21+19+18+17+8+4+2+1, 23+21+19+18+17+8+5+2+1, 23+21+19+18+17+8+5+4+1, 23+21+19+18+17+8+5+4+2+1, 23+21+19+18+17+8+7+6+2+1, 23+21+19+18+17+8+7+6+4+1, 23+21+19+18+17+8+7+6+4+2+1, 23+21+19+18+17+8+7+6+5+2+1, 23+21+19+18+17+8+7+6+5+4+1,

23+21+19+18+17+8+7+6+5+4+2+1, 23+21+19+18+17+10+2+1, 23+21+19+18+17+10+4+1, 23+21+19+18+17+10+4+2+1, 23+21+19+18+17+10+5+2+1, 23+21+19+18+17+10+5+4+1, 23+21+19+18+17+10+5+4+2+1, 23+21+19+18+17+10+8+2+1, 23+21+19+18+17+10+8+4+1, 23+21+19+18+17+10+8+4+2+1, 23+21+19+18+17+10+8+5+2+1, 23+21+19+18+17+10+8+5+4+1, 23+21+19+18+17+10+8+5+4+2+1, 23+21+19+18+17+10+8+7+6+2+1, 23+21+19+18+17+10+8+7+6+4+1, 23+21+19+18+17+10+8+7+6+4+2+1, 23+21+19+18+17+10+8+7+6+5+2+1, 23+21+19+18+17+10+8+7+6+5+4+1, 23+21+19+18+17+10+8+7+6+5+4+2+1, 23+21+19+18+17+16+15+2+1, 23+21+19+18+17+16+15+4+1, 23+21+19+18+17+16+15+4+2+1, 23+21+19+18+17+16+15+5+2+1, 23+21+19+18+17+16+15+5+4+1, 23+21+19+18+17+16+15+5+4+2+1, 23+21+19+18+17+16+15+8+2+1, 23+21+19+18+17+16+15+8+4+1, 23+21+19+18+17+16+15+8+4+2+1, 23+21+19+18+17+16+15+8+5+2+1, 23+21+19+18+17+16+15+8+5+4+1, 23+21+19+18+17+16+15+8+5+4+2+1, 23+21+19+18+17+16+15+8+7+6+2+1, 23+21+19+18+17+16+15+8+7+6+4+1, 23+21+19+18+17+16+15+8+7+6+4+2+1, 23+21+19+18+17+16+15+8+7+6+5+2+1, 23+21+19+18+17+16+15+8+7+6+5+4+1, 23+21+19+18+17+16+15+8+7+6+5+4+2+1, 23+21+19+18+17+16+15+10+2+1, 23+21+19+18+17+16+15+10+4+1, 23+21+19+18+17+16+15+10+4+2+1, 23+21+19+18+17+16+15+10+5+2+1, 23+21+19+18+17+16+15+10+5+4+1, 23+21+19+18+17+16+15+10+5+4+2+1, 23+21+19+18+17+16+15+10+8+2+1, 23+21+19+18+17+16+15+10+8+4+1, 23+21+19+18+17+16+15+10+8+4+2+1, 23+21+19+18+17+16+15+10+8+5+2+1, 23+21+19+18+17+16+15+10+8+5+4+1, 23+21+19+18+17+16+15+10+8+5+4+2+1, 23+21+19+18+17+16+15+10+8+7+6+2+1, 23+21+19+18+17+16+15+10+8+7+6+4+1, 23+21+19+18+17+16+15+10+8+7+6+4+2+1, 23+21+19+18+17+16+15+10+8+7+6+5+2+1, 23+21+19+18+17+16+15+10+8+7+6+5+4+1, 23+21+19+18+17+16+15+10+8+7+6+5+4+2+1, 24+2+1, 24+4+1, 24+4+2+1, 24+5+2+1, 24+5+4+1, 24+5+4+2+1, 24+8+2+1, 24+8+4+1, 24+8+4+2+1, 24+8+5+2+1, 24+8+5+4+1, 24+8+5+4+2+1, 24+8+7+6+2+1, 24+8+7+6+4+1, 24+8+7+6+4+2+1, 24+8+7+6+5+2+1, 24+8+7+6+5+4+1, 24+8+7+6+5+4+2+1, 24+10+2+1, 24+10+4+1, 24+10+4+2+1, 24+10+5+2+1, 24+10+5+4+1, 24+10+5+4+2+1, 24+10+8+2+1, 24+10+8+4+1, 24+10+8+4+2+1, 24+10+8+5+2+1, 24+10+8+5+4+1, 24+10+8+5+4+2+1, 24+10+8+7+6+2+1, 24+10+8+7+6+4+1, 24+10+8+7+6+4+2+1, 24+10+8+7+6+5+2+1, 24+10+8+7+6+5+4+1, 24+10+8+7+6+5+4+2+1, 24+16+15+2+1, 24+16+15+4+1, 24+16+15+4+2+1, 24+16+15+5+2+1, 24+16+15+5+4+1, 24+16+15+5+4+2+1, 24+16+15+8+2+1, 24+16+15+8+4+1, 24+16+15+8+4+2+1, 24+16+15+8+5+2+1, 24+16+15+8+5+4+1, 24+16+15+8+5+4+2+1, 24+16+15+8+7+6+2+1, 24+16+15+8+7+6+4+1, 24+16+15+8+7+6+4+2+1, 24+16+15+8+7+6+5+2+1, 24+16+15+8+7+6+5+4+1, 24+16+15+8+7+6+5+4+2+1, 24+16+15+10+2+1, 24+16+15+10+4+1, 24+16+15+10+4+2+1, 24+16+15+10+5+2+1, 24+16+15+10+5+4+1, 24+16+15+10+5+4+2+1, 24+16+15+10+8+2+1, 24+16+15+10+8+4+1, 24+16+15+10+8+4+2+1, 24+16+15+10+8+5+2+1, 24+16+15+10+8+5+4+1, 24+16+15+10+8+5+4+2+1, 24+16+15+10+8+7+6+2+1, 24+16+15+10+8+7+6+4+1, 24+16+15+10+8+7+6+4+2+1, 24+16+15+10+8+7+6+5+2+1, 24+16+15+10+8+7+6+5+4+1, 24+16+15+10+8+7+6+5+4+2+1, 24+18+17+2+1, 24+18+17+4+1, 24+18+17+4+2+1, 24+18+17+5+2+1, 24+18+17+5+4+1, 24+18+17+5+4+2+1, 24+18+17+8+2+1, 24+18+17+8+4+1, 24+18+17+8+4+2+1, 24+18+17+8+5+2+1, 24+18+17+8+5+4+1, 24+18+17+8+5+4+2+1, 24+18+17+8+7+6+2+1, 24+18+17+8+7+6+4+1, 24+18+17+8+7+6+4+2+1, 24+18+17+8+7+6+5+2+1, 24+18+17+8+7+6+5+4+1, 24+18+17+8+7+6+5+4+2+1, 24+18+17+10+2+1, 24+18+17+10+4+1, 24+18+17+10+4+2+1, 24+18+17+10+5+2+1, 24+18+17+10+5+4+1, 24+18+17+10+5+4+2+1, 24+18+17+10+8+2+1, 24+18+17+10+8+4+1, 24+18+17+10+8+4+2+1, 24+18+17+10+8+5+2+1, 24+18+17+10+8+5+4+1, 24+18+17+10+8+5+4+2+1, 24+18+17+10+8+7+6+2+1, 24+18+17+10+8+7+6+4+1, 24+18+17+10+8+7+6+4+2+1, 24+18+17+10+8+7+6+5+2+1, 24+18+17+10+8+7+6+5+4+1, 24+18+17+10+8+7+6+5+4+2+1, 24+18+17+16+15+2+1, 24+18+17+16+15+4+1, 24+18+17+16+15+4+2+1, 24+18+17+16+15+5+2+1, 24+18+17+16+15+5+4+1, 24+18+17+16+15+5+4+2+1, 24+18+17+16+15+8+2+1, 24+18+17+16+15+8+4+1, 24+18+17+16+15+8+4+2+1, 24+18+17+16+15+8+5+2+1, 24+18+17+16+15+8+5+4+1, 24+18+17+16+15+8+5+4+2+1, 24+18+17+16+15+8+7+6+2+1, 24+18+17+16+15+8+7+6+4+1, 24+18+17+16+15+8+7+6+4+2+1, 24+18+17+16+15+8+7+6+5+2+1, 24+18+17+16+15+8+7+6+5+4+1, 24+18+17+16+15+8+7+6+5+4+2+1, 24+18+17+16+15+10+2+1, 24+18+17+16+15+10+4+1, 24+18+17+16+15+10+4+2+1, 24+18+17+16+15+10+5+2+1, 24+18+17+16+15+10+5+4+1, 24+18+17+16+15+10+5+4+2+1, 24+18+17+16+15+10+8+2+1, 24+18+17+16+15+10+8+4+1, 24+18+17+16+15+10+8+4+2+1, 24+18+17+16+15+10+8+5+2+1, 24+18+17+16+15+10+8+5+4+1, 24+18+17+16+15+10+8+5+4+2+1, 24+18+17+16+15+10+8+7+6+2+1, 24+18+17+16+15+10+8+7+6+4+1, 24+18+17+16+15+10+8+7+6+4+2+1, 24+18+17+16+15+10+8+7+6+5+2+1, 24+18+17+16+15+10+8+7+6+5+4+1, 24+18+17+16+15+10+8+7+6+5+4+2+1, 24+21+18+17+2+1, 24+21+18+17+4+1, 24+21+18+17+4+2+1, 24+21+18+17+5+2+1, 24+21+18+17+5+4+1, 24+21+18+17+5+4+2+1, 24+21+18+17+8+2+1, 24+21+18+17+8+4+1, 24+21+18+17+8+4+2+1, 24+21+18+17+8+5+2+1, 24+21+18+17+8+5+4+1, 24+21+18+17+8+5+4+2+1, 24+21+18+17+8+7+6+2+1, 24+21+18+17+8+7+6+4+1, 24+21+18+17+8+7+6+4+2+1, 24+21+18+17+8+7+6+5+2+1, 24+21+18+17+8+7+6+5+4+1, 24+21+18+17+8+7+6+5+4+2+1, 24+21+18+17+10+2+1, 24+21+18+17+10+4+1, 24+21+18+17+10+4+2+1, 24+21+18+17+10+5+2+1, 24+21+18+17+10+5+4+1, 24+21+18+17+10+5+4+2+1, 24+21+18+17+10+8+2+1, 24+21+18+17+10+8+4+1, 24+21+18+17+10+8+4+2+1, 24+21+18+17+10+8+5+2+1, 24+21+18+17+10+8+5+4+1, 24+21+18+17+10+8+5+4+2+1, 24+21+18+17+10+8+7+6+2+1, 24+21+18+17+10+8+7+6+4+1, 24+21+18+17+10+8+7+6+4+2+1, 24+21+18+17+10+8+7+6+5+2+1, 24+21+18+17+10+8+7+6+5+4+1, 24+21+18+17+10+8+7+6+5+4+2+1, 24+21+18+17+16+15+2+1, 24+21+18+17+16+15+4+1, 24+21+18+17+16+15+4+2+1, 24+21+18+17+16+15+5+2+1, 24+21+18+17+16+15+5+4+1, 24+21+18+17+16+15+5+4+2+1, 24+21+18+17+16+15+8+2+1, 24+21+18+17+16+15+8+4+1, 24+21+18+17+16+15+8+4+2+1, 24+21+18+17+16+15+8+5+2+1, 24+21+18+17+16+15+8+5+4+1, 24+21+18+17+16+15+8+5+4+2+1, 24+21+18+17+16+15+8+7+6+2+1, 24+21+18+17+16+15+8+7+6+4+1, 24+21+18+17+16+15+8+7+6+4+2+1, 24+21+18+17+16+15+8+7+6+5+2+1, 24+21+18+17+16+15+8+7+6+5+4+1, 24+21+18+17+16+15+8+7+6+5+4+2+1, 24+21+18+17+16+15+10+2+1, 24+21+18+17+16+15+10+4+1, 24+21+18+17+16+15+10+4+2+1, 24+21+18+17+16+15+10+5+2+1, 24+21+18+17+16+15+10+5+4+1, 24+21+18+17+16+15+10+5+4+2+1, 24+21+18+17+16+15+10+8+2+1, 24+21+18+17+16+15+10+8+4+1, 24+21+18+17+16+15+10+8+4+2+1, 24+21+18+17+16+15+10+8+5+2+1, 24+21+18+17+16+15+10+8+5+4+1, 24+21+18+17+16+15+10+8+5+4+2+1, 24+21+18+17+16+15+10+8+7+6+2+1, 24+21+18+17+16+15+10+8+7+6+4+1, 24+21+18+17+16+15+10+8+7+6+4+2+1, 24+21+18+17+16+15+10+8+7+6+

4+2+1, 24+21+18+17+16+15+10+8+7+6+5+2+1, 24+21+ 18+17+16+15+10+8+7+6+5+4+1, 24+21+18+17+16+15+ 10+8+7+6+5+4+2+1, 24+21+19+18+17+2+1, 24+21+19+ 18+17+4+1, 24+21+19+18+17+4+2+1, 24+21+19+18+17+ 5+2+1, 24+21+19+18+17+5+4+1, 24+21+19+18+17+5+4+ 2+1, 24+21+19+18+17+8+2+1, 24+21+19+18+17+8+4+1, 24+21+19+18+17+8+4+2+1, 24+21+19+18+17+8+5+2+1, 24+21+19+18+17+8+5+4+1, 24+21+19+18+17+8+5+4+2+ 1, 24+21+19+18+17+8+7+6+2+1, 24+21+19+18+17+8+7+ 6+4+1, 24+21+19+18+17+8+7+6+4+2+1, 24+21+19+18+ 17+8+7+6+5+2+1, 24+21+19+18+17+8+7+6+5+4+1, 24+21+19+18+17+8+7+6+5+4+2+1, 24+21+19+18+17+ 10+2+1, 24+21+19+18+17+10+4+1, 24+21+19+18+17+ 10+4+2+1, 24+21+19+18+17+10+5+2+1, 24+21+19+18+ 17+10+5+4+1, 24+21+19+18+17+10+5+4+2+1, 24+21+ 19+18+17+10+8+2+1, 24+21+19+18+17+10+8+4+1, 24+21+19+18+17+10+8+4+2+1, 24+21+19+18+17+10+8+ 5+2+1, 24+21+19+18+17+10+8+5+4+1, 24+21+19+18+ 17+10+8+5+4+2+1, 24+21+19+18+17+10+8+7+6+2+1, 24+21+19+18+17+10+8+7+6+4+1, 24+21+19+18+17+10+ 8+7+6+4+2+1, 24+21+19+18+17+10+8+7+6+5+2+1, 24+21+19+18+17+10+8+7+6+5+4+1, 24+21+19+18+17+ 10+8+7+6+5+4+2+1, 24+21+19+18+17+16+15+2+1, 24+21+19+18+17+16+15+4+1, 24+21+19+18+17+16+15+ 4+2+1, 24+21+19+18+17+16+15+5+2+1, 24+21+19+18+ 17+16+15+5+4+1, 24+21+19+18+17+16+15+5+4+2+1, 24+21+19+18+17+16+15+8+2+1, 24+21+19+18+17+16+ 15+8+4+1, 24+21+19+18+17+16+15+8+4+2+1, 24+21+ 19+18+17+16+15+8+5+2+1, 24+21+19+18+17+16+15+8+ 5+4+1, 24+21+19+18+17+16+15+8+5+4+2+1, 24+21+19+ 18+17+16+15+8+7+6+2+1, 24+21+19+18+17+16+15+8+ 7+6+4+1, 24+21+19+18+17+16+15+8+7+6+4+2+1, 24+21+19+18+17+16+15+8+7+6+5+2+1, 24+21+19+18+ 17+16+15+8+7+6+5+4+1, 24+21+19+18+17+16+15+8+7+ 6+5+4+2+1, 24+21+19+18+17+16+15+10+2+1, 24+21+ 19+18+17+16+15+10+4+1, 24+21+19+18+17+16+15+10+ 4+2+1, 24+21+19+18+17+16+15+10+5+2+1, 24+21+19+ 18+17+16+15+10+5+4+1, 24+21+19+18+17+16+15+10+ 5+4+2+1, 24+21+19+18+17+16+15+10+8+2+1, 24+21+ 19+18+17+16+15+10+8+4+1, 24+21+19+18+17+16+15+ 10+8+4+2+1, 24+21+19+18+17+16+15+10+8+5+2+1, 24+21+19+18+17+16+15+10+8+5+4+1, 24+21+19+18+ 17+16+15+10+8+5+4+2+1, 24+21+19+18+17+16+15+10+ 8+7+6+2+1, 24+21+19+18+17+16+15+10+8+7+6+4+1, 24+21+19+18+17+16+15+10+8+7+6+4+2+1, 24+21+19+ 18+17+16+15+10+8+7+6+5+2+1, 24+21+19+18+17+16+ 15+10+8+7+6+5+4+1, 24+21+19+18+17+16+15+10+8+7+ 6+5+4+2+1, 25, 26, 27+25, 27+26, 28+25, 28+26, 29+25, 29+26, 29+27+25, 29+27+26, 29+28+25, 29+28+26, 30+25, 30+26, 30+27+25, 30+27+26, 30+28+25, 30+28+26, 31+25, 31+26, 31+27+25, 31+27+26, 31+28+25 and 31+28+26.

In the list above, the numbers refer to the embodiments according to their numbering provided hereinabove whereas "+" indicates the dependency from another embodiment. The different individualised embodiments are separated by commas. In other words, "5+2+1" for example refers to embodiment 5) depending on embodiment 2), depending on embodiment 1), i.e. embodiment "5+2+1" corresponds to embodiment 1) further limited by the features of embodiments 2) and 5). Likewise, "9+8+2+1" refers to embodiment 9) depending mutatis mutandis on embodiments 8) and 2), depending on embodiment 1), i.e. embodiment "9+8+2+1" corresponds to embodiment 1) further limited by the features of embodiment 2), further limited by the features of embodiments 8) and 9).

Methods for preparing the starting compound, i.e. the compound of formula I-1 as defined in embodiment 1), are described in the section "Preparation of starting materials" hereafter, while methods for obtaining macitentan from the compound of formula I-2 as defined in embodiment 1) are described in the section "Use of the compound of formula I-2" hereafter.

Preparation of Starting Materials

The preparation of the compound of formula I-1 as defined in embodiment 1) can be performed as described in WO 02/053557 or in Bolli et al., *J. Med. Chem.* (2012), 55, 7849-7861.

In particular, the compound of formula I-1 can be prepared as described in the section "EXAMPLES" (see subsection "Preparations").

Use of the Compound of Formula I-2

The preparation of macitentan starting from the compound of formula I-2 as defined in embodiment 1) can be performed as described in WO 02/053557 or in Bolli et al., *J. Med. Chem.* (2012), 55, 7849-7861.

In particular, macitentan can be prepared starting from the compound of formula I-2 as described in the section "EXAMPLES" (see subsection "Preparations").

ABBREVIATIONS AND TERMS USED IN THIS TEXT

Abbreviations

The following abbreviations are used throughout the specification and the examples:
approx. approximately
aq. aqueous
DCM dichloromethane
DMSO dimethylsulfoxide
EA ethyl acetate
EG ethylene glycol
eq. equivalent(s)
FID Flame Ionisation Detector
GC gas chromatography
Hept heptane
IT internal temperature
LC-MS liquid chromatography—mass spectroscopy
MEK methyl ethyl ketone
MeOH methanol
MIBK methyl iso-butyl ketone
MIPK methyl iso-propyl ketone
MS mass spectroscopy
org. organic
Pd/C palladium on carbon
% a/a percent determined by area ratio
% w/w percent determined by weight ratio
tBu tert-butyl
THF tetrahydrofuran
$t_R$ retention time Definitions of Particular Terms Used in This Text The following paragraphs provide definitions of the various chemical moieties for the compounds according to the invention as well as other particular terms used in this text and are intended to apply uniformly throughout the specification and claims, unless an otherwise expressly set out definition provides a broader or narrower definition:

The term "halogen" refers to fluorine, chlorine, bromine or iodine, and preferably to fluorine or chlorine.

The expression "apolar aprotic organic solvent" refers to a solvent which is not polar and does not have an acidic hydrogen. Representative examples of apolar aprotic organic solvents include toluene, xylenes, Hex, Hept, CHex and MeCHex. Preferred apolar aprotic organic solvents are Hex and Hept, and the most preferred apolar aprotic organic solvent is Hept.

The expression "mixture of apolar aprotic organic solvents" refers to a mixture of apolar aprotic organic solvents as previously defined. Representative examples of mixtures of aprotic solvents include, but are not limited to: a mixture of two solvents selected from the group consisting of toluene, xylenes, Hex, Hept, CHex and MeCHex; or a mixture of toluene, xylenes and a solvent selected from Hex, Hept, CHex and MeCHex.

The expression "room temperature" as used herein refers to a temperature of from 20 to 30° C., and preferably 25° C.

Unless used regarding temperatures, the term "about" or "approximately" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Particular embodiments of the invention are described in the following Examples, which serve to illustrate the invention in more detail without limiting its scope in any way.

EXAMPLES

All temperatures given are external temperatures and are stated in ° C. Compounds were characterized by $^1$H-NMR (400 MHz) or $^{13}$C-NMR (100 MHz) (Bruker; chemical shifts δ are given in ppm relative to the solvent used; multiplicities: s=singlet, d=doublet, t=triplet, p=pentuplet, hex=hextet, hept=heptet, m=multiplet, br.=broad, coupling constants are given in Hz); by LC-MS (Agilent MS detector G1956B with Agilent 1200 Binary Pump and DAD); by ion chromatography; and by GC-FID.

Parameters of the LC-MS Method 1 ("LC-MS1"):

| | |
|---|---|
| Injection volume: | 2 μL |
| Column: | Kinetex C18, 2.6 μm, 2.1 × 50 mm |
| Column flow rate: | 1 mL/min |
| Eluents: | Eluent A: water + 0.08% TFA |
| | Eluent B: MeCN + 0.012% TFA |
| Gradient: | 2.0 min 95% B |
| | 2.8 min 95% B |
| | 3.0 min 5% B |
| Temperature: | 40° C. |
| Detector wavelength | 210 nm |

Parameters of the LC-MS Method 2 ("LC-MS2"):

| | |
|---|---|
| Injection volume: | 2 μL |
| Column: | YMC Pack Pro C18, 3 μm, 150 × 4.6 mm |
| Column flow rate: | 1.5 mL/min |
| Eluents: | Eluent A: water + 0.1% TFA |
| | Eluent B: MeCN + 0.08% TFA |
| Gradient: | 0 min 15% B |
| | 12 min 90% B |
| | 12.1 min 15% B |
| | 15 min 15% B |
| Temperature: | 25° C. |
| Detector wavelength | 225 nm |

Parameters of the Ion Chromatography Method:

| | |
|---|---|
| Injection volume | 50 μL |
| Ion chromatograph | Methrom 733 IC separation center |
| Detector | Refractive Index Detector |
| Pre-column | Bio Rad Carbo-H Refill Cardridges 30 × 4.5 mm |
| Column | Bio Rad Aminex HPX 87H 300 × 7.8 mm |
| Column temperature | Room temperature |
| Eluent | 2 mmol/L aq. sulfuric acid |
| Flow | Isocratic, 0.6 mL/min |
| Chromatogram time | approx. 30 min |

Protocol of the GC-FID Method:

EG reference solutions in MeOH are prepared with the following respective concentrations: 0, 1, 2, 5, 10, 20, 50, 10, 200 and 500 mg of EG per L of MeOH. 0.02 g of the product to be tested is dissolved in 1 mL MeOH. The parameters of the GC-FID device used are the following:

| | |
|---|---|
| Injection volume | 1 mL |
| Column: | BGB WAX 30 m/0.25 mm/0.25 μm |
| Injection temperature | 250° C. |
| Vector gas/flux | He/0.8 ml/min (constant flow) |
| Column temperature | Initial temperature: 60° C. |
| | Temperature escalating by 15° C./min up to 220° C. |
| Final time | 20 min |
| FID | Temperature: 300 'C. |
| | Hydrogen flow: 40.0 mL/min |
| | Air flow: 400.0 mL/min |
| | Mode: constant makeup flow |
| | Makeup flow: 45.0 mL/min |
| | Makeup Gas Type: Helium |

Preparation A: N-(5-(4-bromophenyl)-6-chloropyrimidin-4-yl)propane-1-sulfamide

A.i. Propane-1-sulfamide

Chlorosulfonyl isocyanate (12.3 mL; 0.14 mol; 1.0 eq.) was slowly added to a cold (−35° C.) solution of benzyl alcohol (14.7 mL; 0.14 mol; 1.0 eq.) in DCM (130 mL) over 30 min. A solution of n-propylamine (14 mL, 0.17 mol; 1.2 eq.) and triethylamine (29.5 mL; 0.21 mol; 1.5 eq.) in DCM (35 mL) was slowly added dropwise at −50° C. The mixture was warmed to 20° C. for 2 h. It was washed with water, followed by aq. 33% HCl and water. The mixture was warmed to 30° C. and the layers were separated. The org. phase was washed with a mixture of Et$_3$N (20 mL; 0.14 mol; 1 eq.) and water (50 mL) so that pH>5. THF (85 mL) was added followed by 10% Pd/C (1 g). The reaction mixture was hydrogenated at 25° C. for 6 h under 6 bars of hydrogen. It was filtered over Celite. The volatiles were removed. DMSO (120 mL) was added. The solution of propane-1-sulfamide (100% theoretical yield) thus obtained in DMSO was used as such in the next step.

A.ii. N-(5-(4-bromophenyl)-6-chloropyrimidin-4-yl)propane-1-sulfamide tBuOK (16.0 g; 0.14 mol; 1 eq.) was added to the above prepared cold (5° C.) solution of Intermediate A.i in DMSO. The resulting suspension was heated to 20° C. and stirred for 30 min. 5-(4-bromophenyl)-4,6-dichloropyrimidine (10.7 g; 0.035 mol; 0.25 eq.) was added portionwise and the mixture was heated to 50° C. for 1 h. Water was added. The pH of the solution was adjusted to 4-5 using 33% aq. HCl. The suspension was cooled to 0° C. and stirred for 30 min. It was filtered off, rinsed with a solution of water and MeOH and dried under reduced pressure to yield the title compound as a white solid (12.6 g, 89% yield with respect to 5-(4-bromophenyl)-4,6-dichloropyrimidine).

Preparation B: N-[5-(4-bromophenyl)-6-[(2-[5-bromo-2-pyrimidinyl)oxy]ethoxy]-4-pyrimidinyl]-N'-propylsulfamide (macitentan)

N-(5-(4-bromophenyl)-6-(2-hydroxyethoxy)pyrimidin-4-yl)propane-1-sulfamide (200 g; 0.46 mol; see Example 1) and 5-bromo-2-chloropyrimidine (117 g; 0.60 mol; 1.3 eq.) were dissolved in toluene (3 L) and DMF (400 mL). The reaction mixture was warmed up to 50° C. and toluene (approx. 400 mL) was distilled our under reduced pressure. The mixture was cooled to 0° C. and tBuOK (156 g, 3 eq., 1.38 mol) was added portionwise. It was stirred at 20° C. for 1 h. Water (1 L) was added and the pH of the solution was adjusted to 3-5 using 33% aq. HCl. The mixture was heated to 50° C. and the layers were separated. The org. phase was treated with charcoal at 50° C. and filtered over Celite. The filter cake was rinsed with toluene. At 50° C., water (1 L) was added to the org. layer. The layers were separated. The org. layer was concentrated under reduced pressure to a total volume of 1 L and cooled to 0° C. The solid obtained was filtered off. It was rinsed with toluene and MeOH. The crude material was suspended in EA (1 L) and heated to 50° C. 300 mL of EA were distilled out and MeOH (400 mL) was added. The suspension was cooled down to 0° C. The solid was filtered off, rinsed with MeOH and dried under reduced pressure to afford the title compound as a white solid (225 g; 83% yield).

Reference Example 1

N-(5-(4-bromophenyl)-6-(2-hydroxyethoxy)pyrimidin-4-yl)propane-1-sulfamide

KOtBu (3.4 eq.) was added with caution (exothermic reaction) to a solution of the compound of Preparation A (1 eq.) in EG (4 mL per g of compound of Preparation A). The resulting mixture was heated to 100° C. for 15 h. It was cooled to 50° C. Water (4 mL per g of compound of Preparation A used) and MeOH (2 mL per g of compound of Preparation A used) were added. After stirring for 10 min, the pH of the solution was adjusted to 4 using 32% aq. HCl. It was cooled to 0° C. within 1.5 h and stirred at this temperature for 30 min. It was filtered off. The solid was slurried in MeOH (4 mL per g of compound of Preparation A used) at 20° C. for 10 min. It was filtered off and dried under vacuum at 50° C. for 15 h to yield the title compound as a light beige solid. The experiment was performed a few times using various amounts of compound of Preparation A. The product had NMR data equivalent to those reported in Bolli et al., *J. Med. Chem.* (2012), 55, 7849-7861. Yield range: 79-96%. LC-MS2: $t_R$=8.04 min; purity range: 93.7-97.4% a/a. Residual ethylene glycol (ion chromatography): 650-4600 ppm.

Reference Examples 2 and 3

N-(5-(4-bromophenyl)-6-(2-hydroxyethoxy)pyrimidin-4-yl)propane-1-sulfamide—Work-Up with Ketone Solvents Different from MIBK KOtBu (0.96 g, 8.6 mmol, 3.5 eq.) was added with caution (exothermic reaction) to a solution of the compound of Preparation A (1 g, 2.5 mmol) in EG (5 mL, 89.4 mol, 36 eq.). The resulting mixture was stirred at 100° C. for 15 h. It was cooled to 50° C. 10 mL of the solvent were added followed by 2M HCl (3 mL). The layers were separated and the org. phase was washed twice with water (7 mL) at 20 to 50° C. An aliquot (0.5 mL) of the org. phase was concentrated to dryness. The amount of residual EG was analyzed by $^1$H-NMR in CDCl$_3$. The rest of the org. phase was concentrated to dryness at 50° C. under vacuum to afford the crude title compound. Besides, an aliquot of the org. phase was submitted to a stress test consisting of heating it at 50° C. for 15 h; the decomposition of the product was measured using LC-MS (LC-MS1).

The results obtained with MIPK and MEK are summarised in Table 1 hereafter.

TABLE 1

| Solvent | Yield | Residual EG ($^1$H NMR) | Decomposition (50° C. stress test) |
|---|---|---|---|
| MIPK | 94% | 20000 ppm | 22% |
| MEK | 92% | <1000 ppm | 47% |

Example 1

N-(5-(4-bromophenyl)-6-(2-hydroxyethoxy)pyrimidin-4-yl)propane-1-sulfamide (work-up with MIBK)

KOtBu (0.96 g, 8.6 mmol, 3.5 eq.) was added with caution (exothermic reaction) to a solution of the compound of Preparation A (1 g, 2.5 mmol) in EG (5 mL, 89.4 mol, 36 eq.). The resulting mixture was stirred at 100° C. for 15 h. It was cooled to 50° C. MIBK (10 mL) was added followed by 2M HCl (3 mL). The layers were separated and the org. phase was washed twice with water (7 mL) at 20 to 50° C. An aliquot (0.5 mL) of the org. phase was concentrated to dryness. The amount of residual EG was analyzed by $^1$H-NMR in CDCl$_3$. The rest of the org. phase was concentrated to dryness at 50° C. under vacuum to afford the crude title compound (90% yield). Besides, an aliquot of the org. phase was submitted to a stress test consisting of heating it at 50° C. for 15 h; the decomposition of the product, measured using LC-MS (LC-MS1), amounted to 26%.

The product had NMR data equivalent to those reported in Bolli et al., *J. Med. Chem.* (2012), 55, 7849-7861. The residual EG content based on NMR was about 2000 ppm.

Example 2

N-(5-(4-bromophenyl)-6-(2-hydroxyethoxy)pyrimidin-4-yl)propane-1-sulfamide (Work-Up with MIBK)

A solution of KOtBu (97.0 g, 0.86 mol, 3.5 eq.) in EG (200 mL, 3.6 mol, 14.5 eq.) was added dropwise to a solution of the compound of Preparation A (100 g, 0.25 mol) in ethylene glycol (200 mL, 3.6 mol, 14.5 eq.) so that IT<40° C. The resulting mixture was stirred at 100° C. for 15 h. Upon completion of the reaction (LC-MS control), it was cooled to 20° C. MIBK (1 L) was added. A 40% aq. solution of citric acid monohydrate (300 mL) was added until pH 4 was reached. The layers were separated. The org. phase was washed with water (750 mL) and the layers were separated. Water (750 mL) was added and the mixture was stirred at 50° C. for 5 min. The layers were separated. The org. phase was concentrated under vacuum at 50° C. until 200 mL of MIBK were removed. Hept (650 mL) was added dropwise at 60-65° C. until turbidity was observed at 60-65° C. The mixture was seeded with an analytically pure sample of N-(5-(4-bromophenyl)-6-(2-hydroxyethoxy)pyrimidin-4-yl)propane-1-sulfamide and stirred at 60-65° C. for 30 min. It was allowed to cool to 5° C. within 3 h. It was filtered off, rinsed with a cold MIBK/Hept mixture (400 mL, 1:1) and dried under vacuum at 50° C. to yield the title compound as a white solid (80 g; 75% yield).

The product had NMR data equivalent to those reported in Bolli et al., *J. Med. Chem.* (2012), 55, 7849-7861. The product purity based on the NMR assay was 99% w/w. [M+H]⁻=431 and 433. LC-MS: $t_R$=1.46 min; purity: 98.5% a/a. Residual ethylene glycol (GC-FID): 72 ppm.

Example 3

N-(5-(4-bromophenyl)-6-(2-hydroxyethoxy)pyrimidin-4-yl)propane-1-sulfamide (Reaction In and Work-Up with MIBK)

EG (124 mL, 3.7 mol, 6.0 eq.) was added to a warm (40-50° C.) suspension of the compound of Preparation A (150 g, 0.37 mol) in MIBK (600 mL). Solid KOtBu (114 g, 1.11 mol, 3.0 eq.) was added portionwise so that IT<60° C. The mixture was stirred for 2-3 h at 100-105° C. After completion of the reaction (LC-MS control), it was cooled to 50° C. A 40% aq. solution of citric acid monohydrate (300 mL) was added until pH 4 was reached. The layers were separated. The org. phase was washed with water (450 mL) and the layers were separated. Water (450 mL) was added and the mixture was warmed to 50° C. It was stirred at 50° C. for 5 min. The layers were separated. The org. phase was concentrated under vacuum at 50° C. until 200 mL of MIBK were removed. Hept (800 mL) was added dropwise at 70-75° C. until turbidity was observed. The mixture was seeded with an analytically pure sample of N-(5-(4-bromophenyl)-6-(2 hydroxyethoxy)pyrimidin-4-yl)propane-1-sulfamide and stirred at 60-65° C. for 30 min. It was allowed to cool to 5° C. within 5 h. It was filtered off, rinsed with a cold MIBK/Hept mixture (300 mL, 1:1) and dried under vacuum at 50° C. to yield the title compound as a white solid (121 g; 76% yield).

The product had NMR data equivalent to those reported in Bolli et al., *J. Med. Chem.* (2012), 55, 7849-7861. [M+H]⁺=430 and 432. LC-MS: $t_R$=1.46 min; purity: 98.4% a/a. Residual ethylene glycol (GC-FID): 530 ppm.

The invention claimed is:
1. A process for preparing the compound of formula I-2

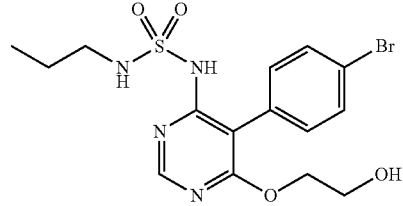

I-2 said process comprising the reaction of the compound of formula I-1

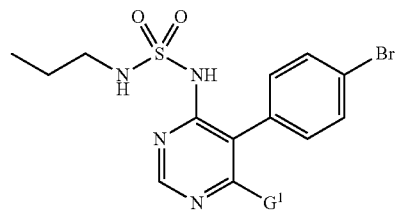

I-1 wherein $G^1$ represents halogen, or a salt of said compound, with ethylene glycol in the presence of a base, wherein after the compound of formula I-2 has been obtained, a liquid-liquid extraction is performed, whereby methyl iso-butyl ketone is used to extract the compound of formula I-2 from an aqueous phase containing the products of the reaction of the compound of formula I-1 with ethylene glycol.

2. A process according to claim 1, wherein $G^1$ represents chlorine.

3. A process according to claim 1, wherein the base is potassium tert-butylate.

4. A process according to claim 1, wherein 20 to 50 equivalents of ethylene glycol are used per equivalent of compound of formula I-1.

5. A process according to claim 1, wherein the pH of the aqueous phase from which the compound of formula I-2 is extracted is between 3 and 5.

6. A process according to claim 1, wherein the reaction of the compound of formula I-1 with ethylene glycol is performed in methyl iso-butyl ketone.

7. A process according to claim 6, wherein the volume of methyl iso-butyl ketone used for performing the reaction of the compound of formula I-1 with ethylene glycol is from 3 to 7 times the volume of ethylene glycol.

8. A process according to claim 6, wherein 5 to 20 equivalents of Ethylene glycol are used per equivalent of compound of formula I-1.

9. A process according to claim 1, wherein the mixture of the aqueous phase and the organic phase is heated to a temperature from 35 to 60° C. before the phases are separated.

10. A process according to claim 1, wherein the compound of formula I-2 obtained after reaction of the compound of formula I-1 with ethylene glycol and the liquid-liquid extraction is crystallised by partial evaporation of methyl iso-butyl ketone from the organic phase collected, addition of an apolar aprotic organic solvent or of a mixture of apolar aprotic organic solvents to said organic phase, heating of the mixture thus obtained until complete solid dissolution is obtained and cooling down the mixture to obtain crystallisation of the compound of formula I-2.

11. A process according to claim 10, wherein the compound of formula I-2 obtained after reaction of the compound of formula I-1 with ethylene glycol and the liquid-liquid extraction is crystallised by partial evaporation of methyl iso-butyl ketone from the organic phase collected, addition of heptane to said organic phase, heating of the mixture thus achieved until complete solid dissolution is achieved and cooling down the mixture to obtain crystallisation of the compound of formula I-2.

12. A process according to claim 1, wherein the proportion of residual ethylene glycol in the compound of formula I-2 obtained is below 500 ppm.

* * * * *